US010285940B2

(12) United States Patent
Mason et al.

(10) Patent No.: US 10,285,940 B2
(45) Date of Patent: May 14, 2019

(54) MULTICOMPONENT, INTERNALLY STRUCTURED NANOEMULSIONS AND METHODS OF PRODUCTION

(71) Applicant: The Regents of the University of California, Oakland, CA (US)

(72) Inventors: Thomas G. Mason, Los Angeles, CA (US); Michael M. Fryd, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/026,537

(22) PCT Filed: Oct. 2, 2014

(86) PCT No.: PCT/US2014/058906
§ 371 (c)(1),
(2) Date: Mar. 31, 2016

(87) PCT Pub. No.: WO2015/051179
PCT Pub. Date: Apr. 9, 2015

(65) Prior Publication Data
US 2016/0235670 A1  Aug. 18, 2016

Related U.S. Application Data

(60) Provisional application No. 61/885,974, filed on Oct. 2, 2013, provisional application No. 61/973,130, filed on Mar. 31, 2014.

(51) Int. Cl.
*A61K 9/107* (2006.01)
*A61K 45/06* (2006.01)
*A61K 9/113* (2006.01)
*A61K 47/18* (2017.01)
*A61K 47/46* (2006.01)

(52) U.S. Cl.
CPC ............ *A61K 9/1075* (2013.01); *A61K 9/107* (2013.01); *A61K 9/113* (2013.01); *A61K 45/06* (2013.01); *A61K 47/186* (2013.01); *A61K 47/46* (2013.01)

(58) Field of Classification Search
CPC ...... A61K 9/107; A61K 9/1075; A61K 9/113; A61K 45/06; A61K 47/186; A61K 47/46
See application file for complete search history.

(56) References Cited

U.S. PATENT DOCUMENTS

2009/0208548 A1   8/2009  Mason et al.
2011/0105629 A1   5/2011  Mason et al.
2012/0128752 A1   5/2012  Loo et al.
2012/0208548 A1 * 8/2012  Park .................... H04W 72/00
                                                                455/452.2

FOREIGN PATENT DOCUMENTS

WO   WO-2009075652   6/2009

OTHER PUBLICATIONS

PubChem, "Ttetrahydrofuran", p. 1; published: Mar. 26, 2005; obtained online: Jan. 8, 2018.*
Chemistry-Dictionary.com, "hydrocarbons", p. 1, obtained online: Jan. 8, 2018.*
International Search Report of International Application No. PCT/US2014/058906.
Becher, P., ed. Encyclopedia of Emulsion Technology; Marcel Dekker, Inc.: New York, 1996.
Bibette et al., Langmuir, 1993, 9, 3352-3356.
Boyd et al., "Factors Affecting Emulsion Stability, and the HLB Concept," J. Colloid Interface Sci. 1971, 41, 359-370.
Chen et al., J. Langmuir, 2002, 18, 7250-7252.
Chen et al., Langmuir, 2009, 25, 4320-4323.
Choi et al., Adv. Mat., 2013, 25, 2536-2541.
Eow et al., "Electrostatic Enhancement of Coalescence of Water Droplets in Oil: A Review of the Current Understanding," Chem. Eng. J 2001, 84, 173-192.
Fainerman et al., Adv. Colloid Interface Sci., 2002, 96, 295-323.
Fryd et al., "Advanced Nanoemulsions," Annu. Rev. Phys. Chem. 2012, 63, 493-518.
Fryd et al., "Nanoinclusions in Cryogenically Quenched Nanoemulsions," Langmuir 2012, 28, 12015-12021.
Fryd et al., "Time-Dependent Nanoemulsion Droplet Size Reduction by Evaporative Ripening," J. Phys. Chem. Lett. 2010, I, 3349-3353.
Fryd et al., Langmuir, 2013, 29, 15787-15793.
Graves et al, Phys. Chem. C, 2008, 112, 12669-12676.
Gutierrez et al., "Nano-Emulsions: New Applications and Optimization of Their Preparation," Curr. Opin. Colloid Interface Sci. 2008, 13, 245-251.
Hafez et al., Biophys J., 2000, 79, 1438-1446.
Hasinovic et al., "One-Step Inversion Process to a Janus Emulsion with Two Mutually Insoluble Oils," Langmuir 2011, 27, 6584-6588.
Herrington et al., Phys. Chem., 1993, 97, 13792-13802.
Jafari et al., "Re-Coalescence of Emulsion Droplets During High-Energy Emulsification," Food Hydrocolloids 2008, 22, 1191-1202.
Jiang et al., "Synthesis of pH-Responsive Particles with Shape Anisotropy," Langmuir 2012, 28, 6760-6768.
Kaler et al., J. Phys. Chem., 1992, 96, 6698-6707.
Kaler et al., Science, 1989, 245, 1371-1374.
Kim et al., Langmuir, 2014, 30, 1473-1488.

(Continued)

*Primary Examiner* — Johann R Richter
*Assistant Examiner* — Genevieve S Alley
(74) *Attorney, Agent, or Firm* — Venable LLP; Henry J. Daley; Miguel A. Lopez

(57) ABSTRACT

The present invention is directed to emulsions with a plurality of droplets dispersed in a continuous liquid medium. These droplets can contain at least a first droplet liquid and a second droplet liquid and can have an ensemble-average maximal spatial dimension that is less than 1 micrometer. The invention includes preparation, uses and compositions containing emulsions. Solute materials can also be dissolved in the droplet liquids.

32 Claims, 9 Drawing Sheets

(56) References Cited

OTHER PUBLICATIONS

Kraft et al., "Self-Assembly of Colloids with Liquid Protrusions," J. Am. Chem. Soc. 2008, 131, 1182-1186.
Leal et al., "Induced Coalescence of Drops in a Viscous Fluid," Phys. Fluids 2004, 16, 1833-1851.
Lee, Colloid Polym. Sc!., 1995, 273, 539-543.
Lucassen-Reynders, J. Colloid Interface Sci., 1981, 81, 150-157.
Manoharan et al., "Dense Packing and Symmetry in Small Clusters of Microspheres," Science 2003, 301, 483-487.
Mason et al., "Nanoemulsions: Formation, Structure, and Physical Properties," J. Phys.: Condens. Matter 2006, 18, R635-R666.
Mayoral et al., "Rotational Fourier Tracking of Diffusing Polygons," Phys. Rev. E 2011, 84, 051405.
Meleson et al., "Formation of Concentrated Nanoemulsions by Extreme Shear," Soft Mater. 2004, 2, 109-123.
Mollet et al., Formulation Technology: Emulsions, Suspensions, Solid Forms, Wiley-VCH, Weinheim, 2001.
Nie et al., J. Am. Chem. Soc., 2006, 128, 9408-9412.
Niu et al., "Electro-Coalescence of Digitally Controlled Droplets," Anal. Chem. 2009, 81, 7321-7325.
Shiloach, Langmuir, 1998, 1998, 1618-1636.
Solans et al., "Nano-Emulsions," Curr. Opin. Colloid Interface Sci. 2005, 10, 102-110.
Tadros et al., "Formation and Stability of Nano-Emulsions," Adv. Colloid Interface Se!. 2004, 108-109, 303-318.
Tan et al., "Droplet Coalescence by Geometrically Mediated Flow in Microfluidic Channels," Microfluid Nanofluid 2007, 3, 495-499.
Taylor, Adv. Colloid Interface Sci., 1998, 75, 107-163.
Tcholakova et al., "Coalescence Stability of Emulsions Containing Globular Milk Proteins," Adv. Colloid Interface Sci. 2006, 123-126, 259-293.
Teh et al., Lab Chip, 2008, 8, 198-220.
Thiam et al., "Adhesive Emulsion Bilayers under an Electric Field: From Unzipping to Fusion," Phys. Rev. Lett. 2011, 107, 068301.
Torza et al., "Effects of the Line Tension on 3-Phase Liquid Interactions," Kolloid-Z u. Z. Polymere 1971, 246, 593-599.
Torza et al., "Three-Phase Interactions in Shear and Electrical Fields," J. Colloid Interface Sci. 1970, 33, 67-83.
Van Aken et al., "Coalescence in llighly Concentrated Coarse Emulsions," Langmuir 2000, 16, 7131-7138.
Wilking et al., Phys. Rev, E, 2007, 75, 041407.
Yatcilla et al., J. Phys. Chem., 1996, 100, 5874-5879.
Zhu et al., Phys. Chem. Chem. Phys., 2012, 14, 2455-2461.

* cited by examiner ns. In the third case, O1 and O2 make contact but full engulfing does not occur, producing an anisotropic O1-O2 singlet droplet having a linear morphology. Such a droplet is also called a "Janus" droplet (i.e. after the two-faced deity of gates in Roman mythology). Many linear Janus droplets dispersed in water form a (O1-O2)/W single emulsion.

MULTICOMPONENT, INTERNALLY STRUCTURED NANOEMULSIONS AND METHODS OF PRODUCTION

CROSS-REFERENCE OF RELATED APPLICATION

This application is a National Stage of International Application No. PCT/US2014/058906, filed on Oct. 2, 2014, which claims priority to U.S. Provisional Applications 61/885,974 filed Oct. 2, 2013 and 61/973,130 filed Mar. 31, 2014, the entire contents of each of which are hereby incorporated by reference.

BACKGROUND

1. Field of Invention

The field of the currently claimed embodiments of this invention relates to methods and compositions for multi-compartment and multicomponent, internally structured nanoemulsions.

2. Discussion of Related Art

Long-lived metastable emulsions contain droplets of a dispersed liquid phase dispersed in a continuous liquid phase. In the presence of quiescent thermal excitations, the dispersed droplets do not recombine or coalesce because repulsions between the droplet interfaces are adequate to stabilize thin films of the continuous liquid phase between the droplets.[1] Typically, the dispersed phase is highly insoluble in the continuous phase, so coarsening of the average droplet size by Ostwald ripening does not occur.[2] However, coalescence of droplets in surfactant- and particle-stabilized emulsions can be induced by a number of means, including raising the osmotic pressure through evaporation of the continuous phase or centrifugation,[3] applying electric fields,[4,5] applying fluid flow,[6,7] changing the surfactant type which affects the hydrophile-lipophile balance (HLB),[8] changing pH,[9] or adding simple salts.[9] In particular, flow-induced coalescence is a physical process in which sufficiently strong fluid flows cause droplets to fuse together, thereby overcoming the stabilizing repulsion between droplet interfaces by causing thinning and rupturing of a film of continuous phase between the droplets.[10] Although detailed real-space studies of flow-induced coalescence of pairs of microscale droplets have been made,[11] relatively little is known about how flow causes both coalescence and rupturing of droplets in emulsions at high droplet volume fractions beyond the dilute regime and at extremely high strain rates required to produce nanoemulsions. Such extreme flows, which may contain extensional and/or shear components, can cause a number of different complex effects such as droplet deformation, non-equilibrium concentration gradients of surfactant on droplet interfaces, and cavitation, all of which could affect droplet coalescence and rupturing rates.

In classic studies by S. Torza and S. G. Mason,[12,13] coalescence between two microscale and larger droplets, each composed of a different immiscible dispersed phase species, has been explored. When a first oil (O1) droplet makes contact with a second different immiscible oil (O2) droplet in water (W), which may contain surfactant, three outcomes are possible; the dominant outcome has the lowest total energy configuration, which can depend on the various liquid-liquid interfacial and line tensions. In the first trivial case, no fusion occurs and the O1 and O2 droplets remain separate. In the second case, the O2 droplet engulfs the O1 droplet, yielding double O1/O2 droplets dispersed in water, also known as an oil-in-oil-in-water O1/O2/W double emulsion. In the third case, O1 and O2 make contact but full engulfing does not occur, producing an anisotropic O1-O2 singlet droplet having a linear morphology. Such a droplet is also called a "Janus" droplet (i.e. after the two-faced deity of gates in Roman mythology). Many linear Janus droplets dispersed in water form a (O1-O2)/W single emulsion.

More recently, emulsions containing microscale and larger Janus droplets have been created using shear and by applying electric fields[14] in combination with flows in microfluidic devices. Janus droplets have also been created inside multiple emulsions.[15] Just as complex structured dispersions of sphere-packed clusters,[16] lithographic colloids,[17] and other anisotropic solid particles[18,19] are receiving increasing attention, structured liquid droplets, such as Janus droplets, are intriguing as potential building blocks for soft materials and for studying interfacial interactions at small scales. Although nanoemulsions consisting of a single or miscible dispersed phases have been studied,[20-23] prior to the approach presented herein, nanoscale linear (O1-O2)/W Janus emulsions, as well as more complex nanoscale variants of compound droplets containing three or more immiscible oils, have not yet been created and studied.

In ionic oil-in-water emulsions, droplets of oil, which have been dispersed in aqueous surfactant solutions by an applied flow, are stabilized against coalescence by adsorbed ionic surfactant molecules on their interfaces. Droplet interfaces in ionic emulsions typically interact through Debye screened-charge repulsions[26] that can provide stability against droplet coalescence even at large droplet volume fractions, $\phi$, through a short-range repulsive barrier in the potential interaction energy between the droplet interfaces. In stable ionic emulsions, the height of this barrier is typically much larger than thermal energy, $k_BT$, where T is the temperature, when the adsorbed surfactant is present in sufficient quantity. If the oil has negligible solubility in the aqueous surfactant solution, then Ostwald ripening[27,2] is suppressed, and, despite being metastable systems in a technical thermodynamic sense, ionic emulsions can persist as stable dispersions for decades without coarsening or noticeable changes in their droplet size distributions.

One example of a highly persistent emulsion is a poly(dimethylsiloxane) (PDMS) silicone oil-in-water (O/W) emulsion stabilized using the anionic surfactant sodium dodecyl sulfate (SDS) near or above its critical micelle concentration (CMC) of about 8 mM.[28] If the molecular weight of the PDMS is sufficiently large, then its solubility in the SDS solution is extremely low, and Ostwald ripening is effectively suppressed. Likewise, because the Debye-screened repulsive interfacial energy barrier provided by the SDS is far in excess of $k_BT$, thermally driven droplet coalescence is negligible. Both microscale and nanoscale PDMS-SDS O/W emulsions have been used as model systems for many studies, including rheology, light scattering, and optical properties because of their excellent long-term stability.[20,29-31]

For ionic emulsions that do not Ostwald-ripen, it is well known that droplet aggregation and coalescence can be induced by adding salt solutions. In classic experiments, simple salts, such as NaCl, have been added to ionic emulsions to induce interfacial attractions[32] and even coalescence between droplets (i.e. "salting out").[33] The presence of the additional dissociated salt ions in the aqueous continuous phase changes the Debye screening length, the potential on the droplet interfaces, and, in some cases, through the common-ion effect, shifts the equilibrium solubility of the surfactant in the solution, thereby altering its Krafft and cloud points.[34] Thus, changes in surfactant phase behavior in response to added simple, non-amphiphilic salts are well known to have an important role in emulsion stability.

Apart from emulsions, mixed ionic surfactant systems have been studied extensively, both experimentally and theoretically, in order to understand their complex phase behavior.[35-37] Such mixed surfactant systems often exhibit synergistic effects and rich phase behavior, arising from the electrostatic attractions between oppositely charged head groups and hydrophobic tails relative to entropic forces. In particular, anionic and cationic surfactant mixtures can cause an increase in surface activity beyond what might be expected based on their individual behavior[38, 39] and double-layer effects can appear to be negligible.[40] Additionally, these mixed systems can form phases composed of molecular dispersions, micelles, vesicles, crystal precipitates, or combinations thereof, depending on the relative concentrations of surfactants and water.[41, 42] Anionic and cationic lipid mixtures can even be used to produce liposomes.[43]

Multi-compartment O/W nanoemulsions, such as Janus and Cerberus nanodroplets, have been produced in a massively parallel process through extreme flow-induced fusion.[44] However, in the absence of strong flow, a surfactant-induced interfacial destabilization process has not yet been used to produce such complex nanoscale droplet structures. Although multi-component compound droplet or particle structures have been created at the microscale, particularly using microfluidics in a serial process,[45-47] three-immiscible-component and higher-order compound droplets have not yet been produced via a massively parallel process at the nanoscale. Moreover, experimental evidence that could provide insight into potential mechanisms causing droplet coalescence and enabling control of droplet fusion in ionic emulsions, which have been destabilized by adding solutions of surfactant salts, is lacking. Thus, studying the behavior of ionic emulsions that are mixed with oppositely charged surfactant solutions, as well as mixtures of two emulsions stabilized by oppositely charged surfactants, would provide a better understanding of interfacial destabilization mechanisms that lead to droplet coalescence and could even provide control over that process.

SUMMARY

Some embodiments of the current invention include an emulsion comprising: a continuous liquid medium; and a plurality of droplets dispersed in said continuous liquid medium, wherein each of said plurality of droplets comprises a first droplet liquid and a second droplet liquid, wherein said first and second droplet liquids are immiscible with each other and immiscible with said continuous liquid medium such that each of said plurality of droplets has at least a first interface of contact between said first droplet liquid and second droplet liquid, and wherein said plurality of droplets has an ensemble-average maximal spatial dimension that is less than 1 μm.

Some embodiments of the current invention include a method of forming an emulsion, comprising: obtaining a first emulsion comprising a first continuous liquid medium and a plurality of first droplets of a first droplet liquid dispersed in said first continuous liquid medium; obtaining a second emulsion comprising a second continuous liquid medium and a plurality of second droplets of a second droplet liquid dispersed in said second continuous liquid medium; mixing said first and second emulsions to provide a mixed emulsion wherein said first and second droplets are stabilized by an interfacial repulsion against forming an interface of contact between said first and second droplet liquids in a common mixed continuous liquid medium while experiencing quiescent thermal excitations; and subjecting said mixed emulsion to an athermal energetic excitation sufficient to overcome an interfacial repulsion between at least a first droplet of said first emulsion and a second droplet of said second emulsion to form a resultant emulsion comprising a plurality of droplets comprising said first droplet liquid and said second droplet liquid having at least a first interface of contact between said first and second droplet liquids, wherein said first and second droplet liquids are immiscible with each other and immiscible with said continuous liquid medium.

Some embodiments of the current invention include a method of forming an emulsion, comprising: obtaining a precursor emulsion, said precursor emulsion comprising: a continuous liquid medium, a first plurality of droplets of a first droplet liquid dispersed in said continuous liquid medium, a second plurality of droplets of a second droplet liquid dispersed in said continuous liquid medium, and one of an anionic amphiphilic agent or a cationic amphiphilic agent; and adding a preselected amount of an ionic agent that is oppositely charged as said one of said anionic amphiphilic agent or said cationic amphiphilic agent such that at least some of said first plurality of droplets and said second plurality of droplets coalesce to provide a resultant emulsion comprising a plurality of coalesced droplets, wherein said first and second droplet liquids are immiscible with each other and immiscible with said continuous liquid medium such that each of said plurality of coalesced droplets has segmented first droplet liquid and second droplet liquid sections.

BRIEF DESCRIPTION OF THE DRAWINGS

Further objectives and advantages will become apparent from a consideration of the description, drawings, and examples.

DETAILED DESCRIPTION

Figure 1:
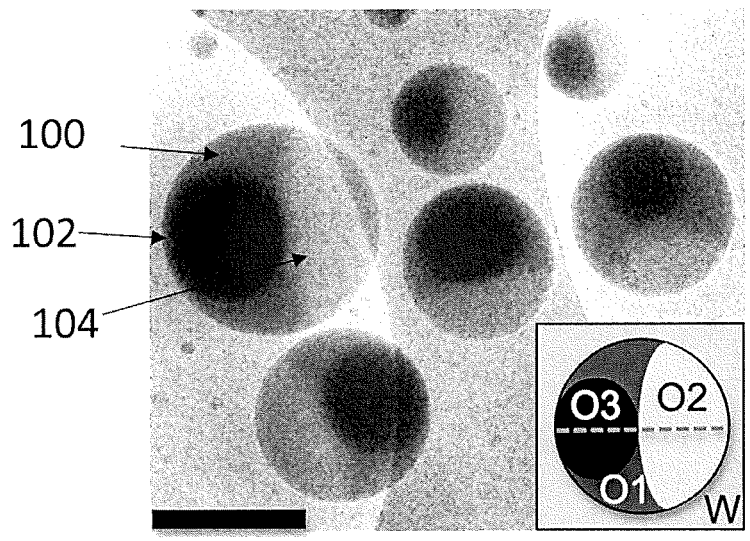
FIG. 1 shows a cryogenic transmission electron microscopy (cryo-TEM) image of engulfed-linear (O3/O1)-O2 Cerberus oil droplets composed of PPPMS (O1, medium gray crescent, 100), POMS (O2, light gray lens, 104), and PFPMS (O3, dark engulfed droplet, 102) created by extreme flow-induced fusion.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

In an embodiment of the invention, we create nanoemulsions composed of internally structured multi-component nanodroplets by flow-induced fusion and rupturing of a mixture of several microscale emulsions, each having different dispersed oil phases that are mutually immiscible and a common continuous aqueous phase. By applying strong athermal excitations, such as can be induced through viscous flows at high flow rates using microfluidic and/or ultrasonic excitation, to premix emulsions containing homogeneous droplets of three different immiscible oils in a common aqueous surfactant solution, we temporarily overcome the interfacial repulsive barrier between droplets created by the surfactant stabilizer molecules, thereby causing multi-droplet fusion without subsequent intermixing of the oils within fused droplets because the oils are immiscible. In some cases, in addition to causing multi-droplet fusion, the strong athermal excitations also cause droplet fission, leading to rupturing of droplets down to overall dimensions in the nanoscale range. Using this highly parallel top-down synthetic approach, we create large-scale quantities of engulfed-linear Cerberus oil-in-water nanoemulsions that have internally structured compartments. Each Cerberus nanodroplet contains three different immiscible oils that form complex-shaped compartments after applying strong athermal excitation, as revealed by cryogenic transmission electron microscopy. Within a given Cerberus nanodroplet, depending upon the interfacial tensions and relative volume fractions of the different oils, the internal oil-oil interfaces can be significantly deformed.

An advantage of some embodiments of the current invention can include a method that can be used to create a deformable liquid delivery vehicle for multiple drug or other molecules that are soluble in only certain oils but not in others. We can create combined nanoscale droplets that ensure that delivery of several different types of drug molecules, which may not all be soluble to a high degree in the same type of oil, are delivered to the same site locally. The overall sub-micron and nanoscale dimensions can make these partitioned multi-component droplets suitable for pharmaceutical applications that would otherwise be out-of-reach for micron-size and larger-scale droplets made by other methods. However, the general concepts of the current invention are not limited to just these examples.

In another embodiment of the invention, we experimentally demonstrate a low-flow method that produces such compartmentalized multi-component oil nanodroplets, as revealed by cryo-TEM measurements. Also, we have generated the first linear 3-component Cerberus nanodroplets; these have a different configuration of internal interfaces than linear-engulfed Cerberus nanoemulsions generated using flow-induced fusion. Having the nanoscale overall radius can make these droplets suitable in pharmaceuticals for drug delivery applications. Moreover, whether at the nanoscale or microscale, we have demonstrated the existence and usefulness of a self-limiting droplet reaction of ionic emulsions that causes droplet fusion and the controlled formation of multi-component nanoemulsions. While examples of fusion of microscale droplets exist through similar anionic-cationic surfactant mixing approaches, e.g. in serial microfluidic devices, our method is massively parallel, so it can offer much higher throughput than such microfluidic devices. Moreover, we extend the approach to the nanoscale and are the first to identify the structure of the fused nanodroplets using cryo-TEM. An embodiment is directed to a material that consists of nanoscale droplets that contain different types of oils in which useful drug molecules of different types may be dissolved. This offers possibilities for localized delivery of different types of oil-soluble drug molecules. We also readily anticipate that a combination of surfactant-induced and flow-induced fusion could be used to create multicompartmentalized oil nanodroplets.

An advantage in some embodiments is that this method can be used to create a deformable liquid delivery vehicle for multiple drug or other molecules that are soluble in only certain oils but not in others, and, by contrast to the flow-induced fusion embodiments also described herein, the process can be carried out in low-flow conditions. We can create combined nanoscale droplets that ensure that delivery of several different types of drug molecules, which may not all be soluble to a high degree in the same type of oil, are delivered to the same site locally. The overall sub-micron and nanoscale dimensions can make these partitioned multi-component droplets suitable for pharmaceutical applications that would otherwise be out-of-reach for micron-size and larger-scale droplets made by other methods. In some cases, a finishing step of separating any surfactant complexes from the emulsion droplets would be needed in the reported herein surfactant-induced approach in order to make a viable pharmaceutical product.

An embodiment of the current invention is directed to a process for making multi-component oil-in-water nanoemulsions by subjecting a premix emulsion of larger droplets of two or more types of immiscible oils, stabilized by a surfactant at low-flow conditions, to high flow rates, typically in a microfluidic homogenizer, causing the droplets to be combined and also ruptured down to the nanoscale. We show that this approach can be used to generate oil nanodroplets that have identifiable compartments and well defined interfaces between different immiscible oils within the same droplet. In particular, we generate new kinds of nanoemulsions: 2 component linear Janus nanodroplets, as well as 3 component linear-engulfed Cerberus nanodroplets. These are different than double W/O/W nanoemulsions (that require special copolypeptides as stabilizers); standard surfactants can be used to make Janus and Cerberus nanoemulsions. Since drug molecules can have vastly different solubilities in different types of oils, we are able to load the oils with several different types of soluble drug molecules, each drug molecule being highly soluble in at least one type of oil. Adding soluble drug molecules to the oils is intended to be included within the scope of the current invention.

Another embodiment of the invention is directed to a process for making multi-component oil-in-water nanoemulsions by combining a premix emulsion of larger droplets of two or more types of immiscible oils, stabilized by an ionic surfactant, with a surfactant solution wherein the amphiphilic species has the opposite charge, causing the droplets to fuse together in a transient self-limiting reaction that provides for re-stabilization of the resulting fused emulsion product. We show that this approach can be used to generate oil nanodroplets that have identifiable compartments and well defined interfaces between different immiscible oils within the same droplet. In particular, we generate nanoemulsions: 2 component linear Janus nanodroplets, as well as 3 component linear Cerberus nanodroplets. These are different than double W/O/W nanoemulsions (that require special copolypeptides as stabilizers); standard ionic surfactants can be used to make Janus and Cerberus nanoemulsions and high flow conditions during mixing of the ionic emulsion and the surfactant solution are not required. Since drug molecules can have vastly different solubilities in different types of oils, we anticipate being able to load the oils with several different types of soluble drug molecules, each drug molecule being highly soluble in at least one type of oil. Adding soluble drug molecules to the oils represents a trivial extension of our basic approach.

EXAMPLES

While Janus droplets may have already been produced at the micron and larger scale, there are no known examples that provide a method of producing them where the overall droplet radius is sub-100 nm. According to some embodiments of the current invention, we experimentally demonstrate a method that produces such droplets, as revealed by cryo-TEM measurements. Also, we have generated the first linear-engulfed 3-component Cerberus droplets, including sub-micron and nanoscale Cerberus droplets. Having a nanoscale overall radius can make these droplets suitable in pharmaceuticals for drug delivery applications.

Example 1: Multicomponent, Internally Structured Nanoemulsions and Methods of Production Flow Method of Producing Multicomponent Nanodroplets Here, we apply extremely strong liquid flows (e.g. shear and/or extensional flows) to overcome the repulsive barrier between mixed microscale droplets of different mutually immiscible oils in aqueous surfactant solutions, causing the droplets to fuse together as they are also being ruptured to nanoscale dimensions. The immiscible oils combine in this highly out-of-equilibrium environment to form compartmentalized multi-component nanodroplets, which remain stable against coalescence after the flow is removed. In particular, we focus on creating and characterizing three-component oil nanodroplets dispersed in water and anionic surfactant. We call such droplets "Cerberus" droplets, naming them after the three-headed dog of Roman mythology that guards the gates of Hades. Using three mutually immiscible siloxane oils that we have identified, we form an engulfed-linear (O3/O1)-O2/W Cerberus nanoemulsion in which a smaller nanodroplet of a third oil phase O3 has been preferentially engulfed inside only the O1 portion of a linear O1-O2 nanodroplet. Interestingly, the O1-O2 lens' interface and the engulfed O3 droplet's interface can be significantly deformed even if the Cerberus droplet as a whole remains nearly spherical. Depending on the relative volumes of each oil type within a given nanodroplet as observed using cryo-TEM, we classify different degrees of deformation of the O3 engulfed droplet as well as changes in the curvature of the lens between the O1-O2 phases. We explain many of the structural features of the Cerberus nanodroplets in terms of the measured interfacial tensions between six pairs of four immiscible liquids using equilibrium arguments, but some of the features reflect the out-of-equilibrium process used to create the nanodroplets in combination with line tension effects.

Results and Discussion

Examples of compartmentalized Cerberus oil droplets created using extreme-flow applied to a mixed microscale emulsion containing three different immiscible oils (see Materials and Methods) are shown in the cryo-TEM image of FIG. 1. Structure-free regions outside the droplets confirm that the ice is vitreous; nanoinclusions of gas within the oil droplets[24] are not observed. Each multi-component Cerberus droplet is nearly spherical and contains three distinctly different oil regions (PPPMS=O1, POMS=O2, and PFPMS=O3), which can be differentiated because of differences in electron density. Assuming that differences in electron density correspond to differences in mass density, we infer that the lightest gray lens within a droplet is POMS, the medium gray crescent region is PPPMS, and the darkest region is PFPMS. For clarity in defining the various compartments, the droplets displayed in FIG. 1 have sub-micron dimensions. Similar engulfed-linear (O3/O1)-O2 Cerberus oil droplets are also seen in other cryo-TEM images down to nanoscale (i.e. sub-100 nanometer) overall dimensions.

FIG. 1 shows a cryogenic transmission electron microscopy (cryo-TEM) image of engulfed-linear (O3/O1)-O2 Cerberus oil droplets composed of PPPMS (O1, medium gray crescent, 100), POMS (O2, light gray lens, 104), and PFPMS (O3, dark engulfed droplet, 102) created by extreme flow-induced coalescence. The continuous phase outside the droplets is vitreous ice (W). Equal volumes of each oil type have been emulsified; the total overall oil volume fraction $\phi_T$ during emulsification is $\phi_T$=0.3. The resulting emulsion is diluted before taking the cryo-TEM image. The large gray hourglass-shaped area extending from the top to the bottom in the middle of the image is part of the TEM grid. Scale bar is 500 nm. Inset: schematic cross-sectional view of an engulfed-linear (O3/O1)-O2 Cerberus droplet having a single axis of symmetry, shown by the dashed line. The continuous phase of aqueous surfactant solution is labeled as W.

Nearly all observed Cerberus droplets in the 2D cryo-TEM images have a single axis of symmetry that passes through the center of the convex-convex lens of O2, the concave-convex lens of O1, and the engulfed droplet of O3 in O1 (see the dashed yellow line in FIG. 1 inset). If O3 had instead formed a lens on the surface of O1, rather than being engulfed, then the O3 lens would not always be centered along the same axis of symmetry as the lens of O2. In other words, random thermal motion of an O3 lens relative to the axis defined by the O2 lens would make many observations of a single symmetry axis in a large number of Cerberus droplets extremely unlikely. By contrast, an O3 droplet that is engulfed in O1 and confined by the convex-concave boundaries of O1 would share a single symmetry axis with the lens of O2. Thus, the O3 droplet is engulfed entirely within the O1 region. For some Cerberus droplets, a slight prolate elongation of the outer boundary is observed along the symmetry axis. Presumably, this elongation, typically five percent or less, arises from the presence of internal oil-oil interfaces.

Figures 2A, 2B, 2C:
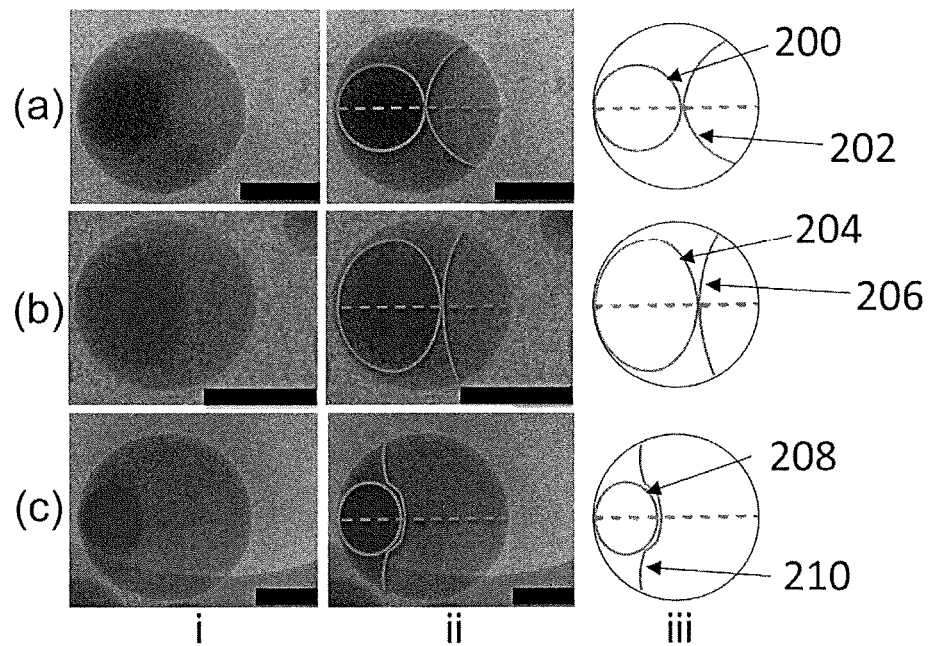
FIGS. 2A-2C show three different qualitative geometries observed in cryo-TEM micrographs of engulfed-linear Cerberus droplets composed of PFPMS, PPPMS, and POMS.

Although a single axis of symmetry is observed for the vast majority of Cerberus droplets, there is some variation in the relative internal volumes of the three oils. These variations are most likely a consequence of different particular sequences of droplet fusion and fission events during high flow; they give rise to several qualitatively different deformation geometries of the internal oil-oil interfaces. In FIGS. 2A-2C, we categorize a wide range of observed droplet geometries into three qualitatively different types. In the first geometry, denoted spherical-convex or SC (FIG. 2A), the engulfed O3 droplet is spherical (200) and the O2 lens' interfacial curvature is convex (202). In the second geometry, denoted deformed-convex or DC (FIG. 2B), the engulfed O3 droplet is deformed (204) and the O2 lens is convex (206), although the lens may be somewhat deformed. In the third geometry, denoted deformed-concave-convex or DCC (FIG. 2c), the engulfed droplet (208) is deformed and the lens is dimpled at its center, yielding concave curvature near the symmetry axis but convex curvature near the O1-O2-water contact line.

FIGS. 2A-2C show three different qualitative geometries observed in cryo-TEM micrographs of engulfed-linear Cerberus droplets composed of PFPMS, PPPMS, and POMS. FIG. 2A shows Cerberus SC droplet having spherical engulfed droplet (200) and convex internal interfacial curvature of the lens (202). FIG. 2B shows Cerberus DC droplet having a deformed engulfed droplet (204) and convex interfacial curvature of the lens (206). FIG. 2C shows Cerberus DCC droplet having deformed engulfed droplet (208) and dimpled lens (210) having both concave and convex curvatures. The dark region extending the length of the micrograph bottom is part of the TEM grid. Columns: (i) cryo-TEM image of Cerberus droplets, (ii) profile lines of internal oil-oil interfaces are superimposed for clarity, and (iii) schematic showing only interfaces based on (ii). Dashed lines: symmetry axis. Scale bar: 250 nm.

Figures 3A, 3B:
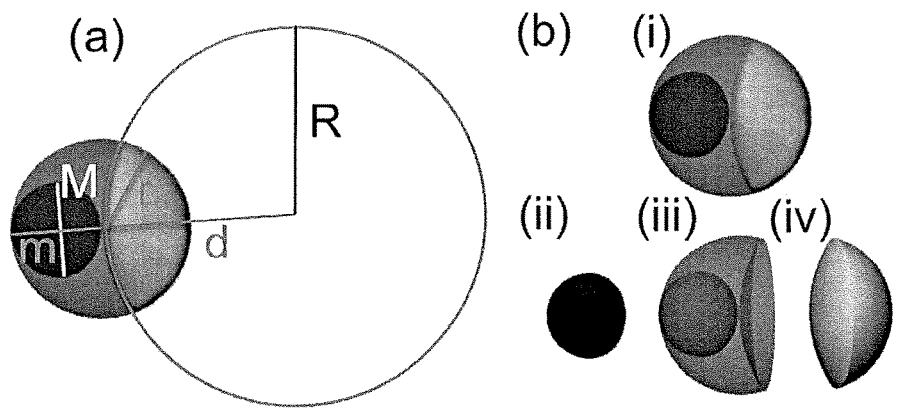
FIGS. 3A-3B show engulfed-linear Cerberus (O3/O1)-O2 droplet analysis model used to extract oil phase volumes from micrographs.

To quantify the individual volumes of each of the oils inside a Cerberus droplet from a cryo-TEM micrograph, we have developed the following model. For simplicity, we only consider and analyze droplets oriented in profile, having their symmetry axes in the plane of observation. Moreover, we ignore any slight prolate elongation and assume that a Cerberus droplet is a sphere having radius, r, corresponding to a total droplet volume $V_T = (4\pi/3)r^3$. We also assume that the internal curvature of the O2 lens is well approximated by an imaginary sphere having radius R (FIG. 3A). The distance between the centers of the two spheres is d. A sphere-sphere intersection volume then approximates the volume of the lens $V_{O2}$ (FIG. 3B iv):

$$V_{O2} = \frac{\pi(d^2 + 2rd + 2Rd + 6rR - 3r^2 - 3R^2)(r + R - d)^2}{12d}.$$

Next, although the engulfed droplet of O3 can have a complex asymmetric geometry, O3 is estimated by assuming an oblate ellipsoid shape and measuring the major axis, M, and minor axis, m (FIG. 3A). The engulfed droplet volume (FIG. 3B ii) is then given by $V_{O3} \approx (\pi/6)\,mM^2$. The remaining volume $V_{O1}$ of the complex shape of O1 (FIG. 3B iii) is obtained from $V_{O1} = V_T - V_{O2} - V_{O3}$. The compartmentalized oil phase volume fractions, $\psi_{O1}$, $\psi_{O2}$, and $\psi_{O3}$, within a given droplet are determined by dividing their respective oil volumes by the total droplet volume $V_T$.

FIGS. 3A-3b show engulfed-linear Cerberus (O3/O1)-O2 droplet analysis model used to extract oil phase volumes from micrographs, assuming that the droplet is in profile (i.e. a single symmetry axis of revolution lies in the image plane). FIG. 3A shows the definition of variables needed to extract volumes. FIG. 3b shows the individual volume components. (i) Total droplet volume is approximated by a sphere of radius r. (ii) O3 droplet volume is approximated by volume of oblate ellipsoid using M and m. (iii) O1 volume is approximated by subtracting all other volumes from $V_T$. (iv) O2 lens volume is approximated by the overlapping sphere-sphere volume intersection using r, R, and d.

Figure 4:
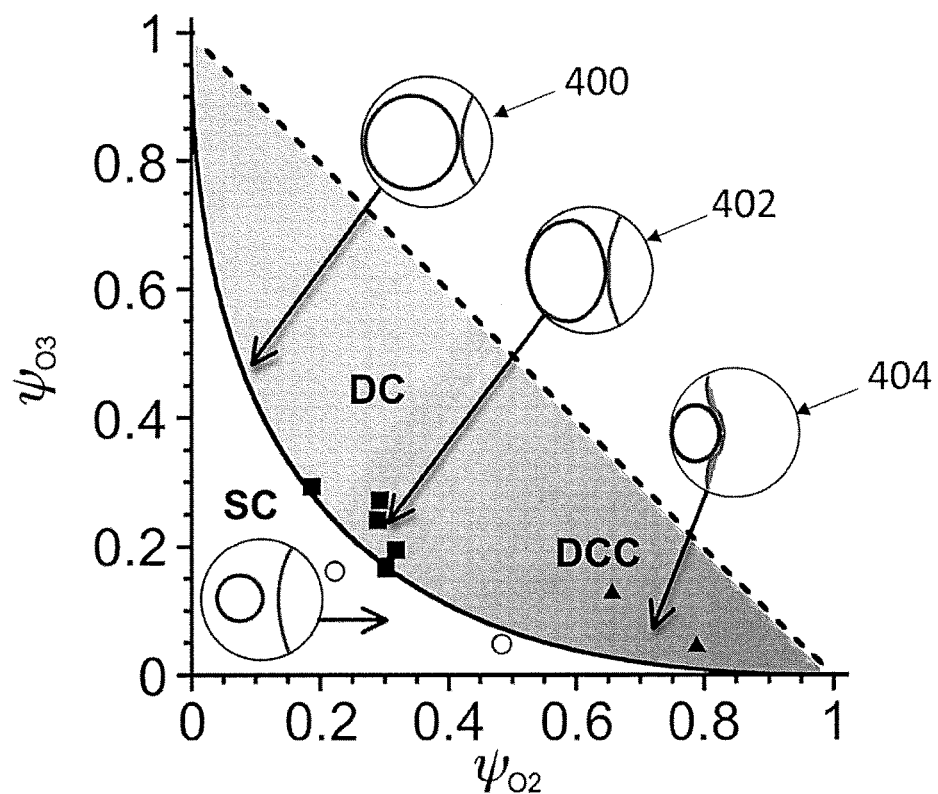
FIG. 4 shows results of image analysis of engulfed-linear Cerberus droplets in profile, plotted in a space of dimensionless internal oil phase relative volumes ($\psi_{O2}, \psi_{O3}$).

FIG. 4 presents volume analysis results from droplets in profile observed in several cryo-TEM images. The dashed line, corresponding to $\psi_{O2} + \psi_{O3} = 1$, is the upper boundary where $\psi_{O1}$ is zero. The three qualitatively different interfacial geometries of engulfed-linear Cerberus droplets are shown (400, 402 and 404). Undeformed engulfed droplets (SC) are shown as open symbols and deformed engulfed droplets (DC and DCC) are shown as solid symbols. As $\psi_{O2}$ becomes large, the O2 lens becomes dimpled and the Cerberus droplets have a DCC geometry rather than DC.

More specifically, FIG. 4 shows results of image analysis of engulfed-linear Cerberus droplets in profile, plotted in a space of dimensionless internal oil phase relative volumes ($\psi_{O2}$, $\psi_{O3}$). Symbols denote analyzed results from cryo-TEM micrographs having SC (○), DC (■), and DCC (▲) geometries. The solid back line represents the maximum relative spherical engulfed droplet volume $\psi_{O3}^*$ for a given $\psi_{O2}$ according to the model presented in the text. The black dashed line $\psi_{O2} + \psi_{O3} = 1$ represents the limit as $\psi_{O1}$ approaches zero, since volume conservation requires $\psi_{O1} + \psi_{O2} + \psi_{O3} = 1$. Droplet schematics in the style of FIGS. 2a-2c show a representation of how a Cerberus droplet would appear at the location shown. Geometry phase spaces are white for SC, light gray for DC, and dark gray for DCC.

A simple model of engulfed-linear Cerberus oil droplets predicts the ranges of $\psi_{O2}$ and $\psi_{O3}$ over which deformation of the engulfed O3 droplet and the O2 lens will occur as a result of their interaction. Averaging over Cerberus droplets observed in profile, we find R/r≈1.4, so we fix this ratio, recognizing that this approximation would be most appropriate for SC and DC cases. For a given value of $\psi_{O2}$, we calculate d and thus the volume of the biconvex O2 lens. Assuming that the engulfed O3 droplet is spherical, we vary $\psi_{O3}$, corresponding to its volume, and determine the value $\psi_{O3}$* at which it just makes contact with the undeformed O2 lens. The lower boundary line $\psi_{O3}$*($\psi_{O2}$) is plotted in FIG. 4. This model reasonably estimates the boundaries defining deformation of the observed internal oil-oil interfaces within a Cerberus droplet. Because R/r of the model is chosen to be an average, this model provides only a guideline and can be further refined by using measured values of r and R for individual droplets.

Using cryo-TEM, we have also verified that separate and identifiable internal compartments are not produced when using the same extreme flow process on premixed emulsions that contain droplets of two or more different miscible oils.[24] When the oils are miscible, no internal compartments are seen within the outer boundary of the droplet; the interiors of the droplets appear uniformly gray. Flow-induced coalescence of such miscible droplets enables their contents to intermix, and this accounts for the absence of internal compartments.

Beyond engulfed-linear Cerberus droplets, the full range of possible multi-component droplet morphologies depends on the interfacial and line tensions between the various immiscible phases. Currently, no theory predicts a priori which droplet morphologies will be seen for a three-component system having immiscible oil phases when all relevant interfacial and line tensions are known. Such a theory would be especially useful, since not all 3-component immiscible oil combinations would be expected to produce only engulfed-linear Cerberus morphologies. The interfacial and line tensions must be such that the immiscible oils must all prefer to be wet by each other, at least in part, as compared to being wetted by the continuous phase. If this is not the case, then a particular phase might be expelled from a droplet regardless of forced flow-induced coalescence. Restricting consideration to three mutually immiscible oil phases that are fused by flow in a continuous phase of an aqueous surfactant solution, we predict that it is possible in principle to create seven different morphologies, including several different types of multiple emulsions (see FIGS. 5A-5G).

Figures 5A, 5B, 5C, 5D, 5E, 5F, 5G:
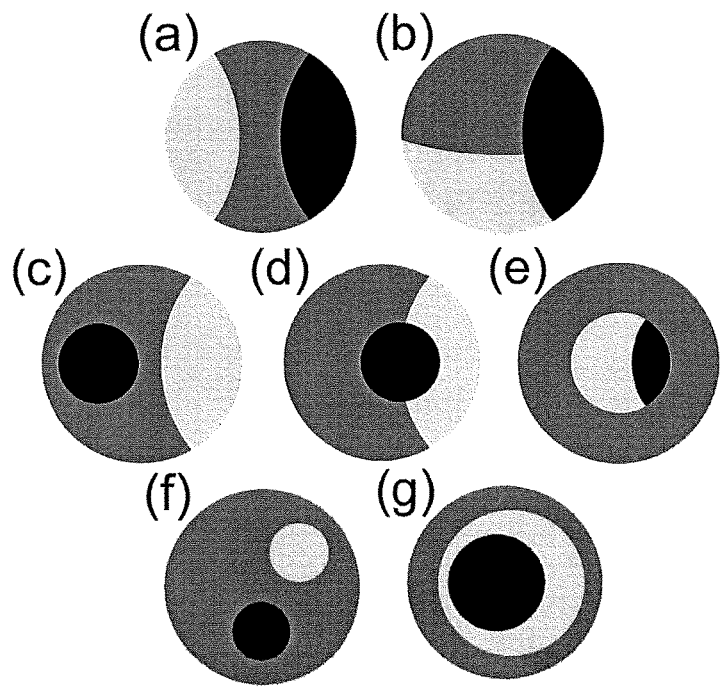
FIGS. 5A-5G show schematic cross-sections of predicted possible Cerberus droplet morphologies containing three immiscible oils.

FIGS. 5A-5G show schematic cross-sections of predicted possible Cerberus droplet morphologies containing three immiscible oils. Different morphologies correspond to different interfacial and line tensions between all phases: O1 (lightest gray), O2 (medium gray), O3 (black), and W (white). FIG. 5A shows a linear singlet O1-O2-O3 droplet. FIG. 5B shows a fan singlet O1-O2-O3-droplet. FIG. 5c shows an engulfed-linear double (O3/O1)-O2 droplet (dominant experimentally observed morphology for the set of oils we have used). FIG. 5D shows a linear-shared-engulfed O3/(O1-O2) droplet. FIG. 5E shows an engulfed Janus double (O2-O3)/O1 droplet. FIG. 5F shows a double separate engulfed (O1,O3)/O2 droplet. FIG. 5G shows a triple O3/O1/O2 droplet. Nomenclature: "/" means inside; "-" means in contact with; "," means not in contact with; and a trailing "-" means also in contact with the first oil listed.

Our measurements of six different interfacial tensions (W-O1, W-O2, W-O3, O1-O2, O1-O3, and O2-O3), as described in the Materials and Methods section, provide some insight into the preference of the engulfed-linear Cerberus droplet structure for the particular set of oils we have used in our experiment. The O1-O2 interfacial tension ($\sigma_{O1-O2}$=2.9 dyn/cm) is significantly smaller than any other. Once O1/W droplets have coalesced with O2/W droplets as a result of flow overcoming the interfacial repulsion, increasing O1-O2 interfacial area while simultaneously reducing W-O1 and W-O2 interfacial areas would be preferred even during subsequent rupturing. Thus, the low value of $\sigma_{O1-O2}$ accounts for the predominantly linear structure between O1 and O2, consistent with the observed convex-concave and convex-convex lens structures of these two oils, in the linear-engulfed Cerberus droplets. Because all of the water-oil interfacial tensions are significantly larger than $\sigma_{O1-O2}$, the exterior shape of the droplets remain nearly spherical, and only small distortions away from spherical arise from the internal O1-O2 interface. The O2-O3 interfacial tension ($\sigma_{O2-O3}$=21.0 dyn/cm) is higher than any of the others, so minimizing the contact area between O2 and O3 is energetically favorable. Thus, any fluorinated oil O3 inside the Cerberus droplet would prefer to be entirely engulfed in O1 rather than make contact with O2. Because $\sigma_{O1-O3} \gg \sigma_{O1-O2}$, the O1-O2 internal interface (associated with the lens of O2) will have a greater propensity to deform, and this accounts for the wrap-around and dimpled structures observed for the O1-O2 internal interfaces as well as the relatively smaller deformations of engulfed O3 droplets.

However, because $\sigma_{O1-O3}$ (15.4 dyn/cm) is slightly larger than $\sigma_{W-O3}$ (12.0 dyn/cm), there appears to be a driving force that would favor the expulsion of the engulfed O3 droplet into the W phase. Thus, a question remains about why a spherical engulfed O3/O1 droplet is not simply expelled from the Cerberus droplet into the aqueous phase to create a spherical O3/W droplet instead. We hypothesize that this does not occur for the following two reasons: (1) the W-O1-O3 line tension and energy that would be associated with creating a contact line as an O3 droplet emerges from O1 into W effectively prevents the O3 droplet from leaving the O1 phase and entering the W phase, and/or (2) the O3 droplet leaving the O1 oil would not be immediately populated with fluorinated surfactant as it emerges, so its instantaneous non-equilibrium interfacial tension $\sigma_{W-O3}$* would be actually higher as a bare droplet in the W phase than the measured equilibrium value of $\sigma_{W-O3}$ and also $\sigma_{O1-O3}$. Additional experiments, beyond the scope of this work, would be necessary to investigate these hypotheses.

A careful inspection of the cryo-TEM images indicates that the O3 droplet in the DC and DCC geometries can be deformed in a manner that is not completely symmetric. The engulfed O3 droplet has a convex O1-O2 lens pressing it on one side and a concave O1-W interface pressing it on the opposite side (FIG. 2b). Thus, the deformed engulfed O3 droplet appears to be oblate ovoidal, not simply oblate spheroidal; it is less deformed near the concave O1-W interface and more deformed near the convex O1-O2 interface. As the engulfed O3 droplet presses against the O2 lens, the interfacial curvature between O1 and O2 also changes. While using a spheroidal model of the engulfed O3 droplet is adequate to capture its primary deformation, using an ovoidal model could provide a more accurate description of its true interfacial structure.

Conclusion

One can also explore a phase space of initial compositions that is wider than what we have surveyed thus far in particular examples. By fixing the multi-component premix emulsions to have equal volumes of each oil phase, the majority of the Cerberus droplets that we have created and observed are, not surprisingly, found near $\psi_{O1}=\psi_{O2}=\psi_{O3} \approx 1/3$. By changing the relative volumes of each oil phase in the mixed premix emulsion, one might fully explore and map out the boundary between the DC and DCC geometries. Likewise, it would be useful to develop a more sophisticated theory that fully describes the three-dimensional geometries (e.g. ovoidal compressed engulfed droplets) of the compartmentalized oils within nanodroplets after flow-induced fusion and rupturing. Further interpretation of the images of Cerberus droplets may lead to a method of estimating or measuring line tensions, which could play a role in influencing the resulting morphologies and metastable configurations of interfacial structures inside multi-component nanoscale droplets after this highly non-equilibrium process.

We have shown that extreme liquid flow can be used to overcome the repulsive barrier between droplets of three mutually immiscible oils in an aqueous surfactant solution, thereby forcing the droplets to fuse together while also being rupturing to nanoscale dimensions. This complex process results in three-component Cerberus nanodroplets that remain stable against coalescence after the flow is removed. For the particular choice of three different siloxane oils that we have used in our experiments, the resulting Cerberus oil droplets have clear internal compartmentalization and an engulfed-linear morphology. Depending on the relative oil volumes within a droplet, the internal interfaces of the engulfed O3 droplet and the O2 lens can be deformed as these interfaces interact, leading to an ovoidal shape of the engulfed O3 droplet and dimpling of the O2 lens. By completely eliminating the O3 oil in the composite premix emulsion prior to high-flow emulsification (i.e. by using only two oils O1 and O2), we have also created large-scale quantities of two-component nanoscale Janus (O1-O2)/W emulsions. The extreme flow-induced droplet fusion and rupturing method that we have developed for two or three oils can be readily applied to higher numbers of immiscible oils, leading to even more complex nanodroplets having multi-compartment internal morphologies.

Materials and Methods

Nanoemulsion Formation.

Figures 6A, 6B:
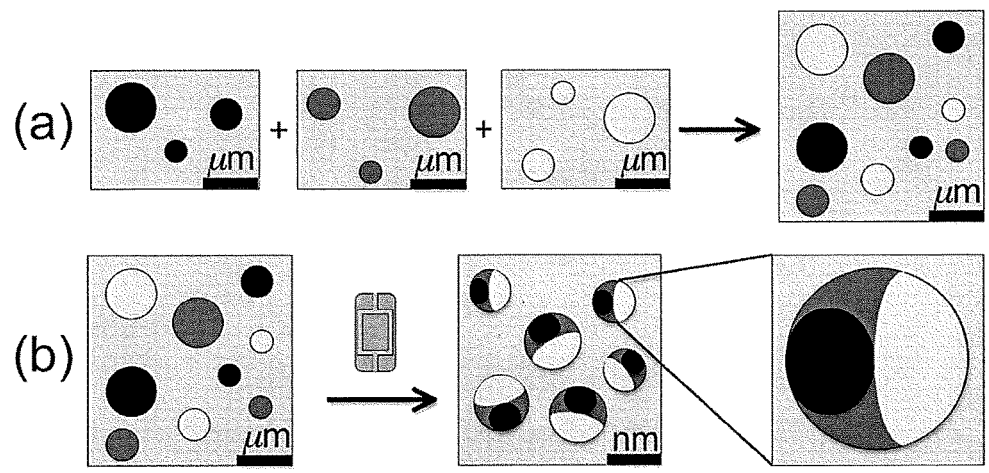
FIGS. 6A-6B show a schematics of flow-induced Cerberus nanodroplet formation using three mutually immiscible oils: gray=O1, white=O2, black=O3.

Three mutually immiscible poly(siloxane) oils, determined by miscibility screening studies at room temperature and atmospheric pressure, are: poly(2-phenylpropylmethylsiloxane) (PPPMS=O1, mass density $\rho_{PPPMS}$=1.02 g/mL), poly(octylmethylsiloxane) (POMS=O2, $\rho_{POMS}$=0.91 g/mL), and poly(3,3,3-trifluoropropylmethylsiloxane) (PFPMS=O3, $\rho_{PFPMS}$=1.28 g/mL), obtained from Gelest. A Fisher Scientific Power Gen 125 rotary mixer is used to create three separate microscale polydisperse oil-in-water emulsions, one for each type of mutually immiscible oil: O1/W, O2/W, and O3/W (FIG. 6A left). Each microscale premix emulsion is made at the same oil droplet volume fraction, $\phi$=0.3 and aqueous anionic sodium dodecyl sulfate (SDS) surfactant concentration $C_{SDS}$=5 mM. An anionic fluorinated surfactant solution (Masurf FS-615) is also added to the PFPMS emulsion at 0.3% v/v for additional stabilization of the PFPMS.

Next, each of the three different microscale anionically stabilized oil-in-water emulsions are gently mixed together in equal volumes, so no droplet rupturing or coalescence occurs; thus, the total overall oil droplet volume fraction in the mixed microscale emulsion is $\phi_T$=0.3 (FIG. 6A, right). This mixed microscale emulsion is subjected to extreme-flow emulsification using a hard microfluidic homogenizer (M-110P Microfluidizer using a 75 μm Y-type diamond interaction chamber) at a peak liquid pressure of $p_1$=25,000 psi (FIG. 6B). Because flows in the homogenizer are spatially and temporally inhomogeneous, the resulting complex nanoemulsion is re-circulated through the homogenizer N=15 times in order to ensure that all nanodroplets have experienced the same peak-flow conditions and have a more uniform overall radial droplet size distribution.[25]

FIGS. 6A-6B show a schematics of flow-induced Cerberus nanodroplet formation using three mutually immiscible oils: gray=O1, white=O2, black=O3. FIG. 6A shows three separate microscale emulsions are combined at room temperature to form a mixed microscale emulsion. Representative scale bar ≈10 μm. FIG. 6B shows mixed microscale emulsion is subjected to extreme-flow, causing droplet fusion and rupturing. After N≥1 passes, this process yields a Cerberus nanoemulsion of type O3/O1-O2/W for oils we use. The continuous phase of aqueous surfactant solution is shown in each of the panels to encompass each of the immiscible oils and nanodroplets. Detail (right): oil regions inside a near-spherical nanodroplet. Symbol above arrow in (b): high-flow emulsification in a hard microfluidic device. Representative scale bar ≈200 nm.

Cryogenic Transmission Electron Microscopy.

Figure 7:
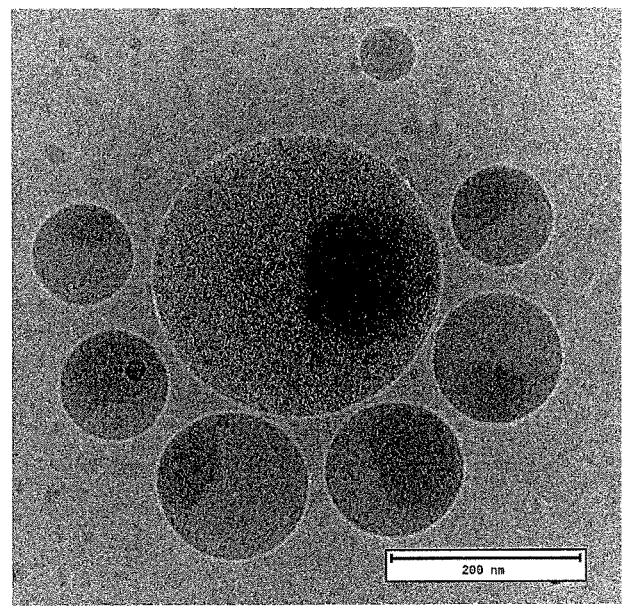
FIG. 7 is a C-TEM image of nanoscale Cerberus 3-oil-component droplets dispersed in an aqueous 5 mm SDS solution created by an embodiment of the current invention.

To image nanoscale droplets, cryogenic transmission electron microscopy (cryo-TEM) is employed. We use a previously developed cryo-TEM sample preparation and microscopy procedure with a FEI Tecnai $G^2$ TF 20 transmission electron microscope.[24] Care is taken to quench the temperature in a manner that yields high-quality vitreous ice, thereby eliminating the formation of nanoinclusions that could otherwise complicate interpretation of the images. In order to enhance contrast between the different oil regions within droplets, cryo-TEM images are high-pass filtered and their levels are adjusted. An example image of linear-engulfed Cerberus nanodroplets of three different immiscible oils fused together in an aqueous surfactant phase is shown in FIG. 7. This image demonstrates the production of Cerberus droplets having radii that are sub-100 nm, so these droplets lie in the regime of nanodroplets of nanoemulsions.

FIG. 7 is a C-TEM image of nanoscale Cerberus 3-oil-component droplets dispersed in an aqueous 5 mm SDS solution created by an embodiment of the current invention. With the exception of the largest central droplet, all droplets shown have sub-100 nm radii, so they are nanoscale droplets. Each Cerberus droplet has a biconvex lens of O2 (POMS) in contact with a concave-convex lens of O1 (PPPMS), and a smaller droplet of O3 (FPMS) engulfed within O1.

In an alternative embodiment of the current invention, we have made a composite premix emulsion containing droplets of only two immiscible oils O1 and O2, but not O3, in an aqueous 5 mM SDS solution and have subjected it to high-flow emulsification using a microfluidizer, thereby producing a O1-O2/W Janus nanoemulsion. By controlling the liquid pressure setting on the microfluidizer, we have adjusted the peak flow rate, and we thereby change the overall maximum dimension of the Janus droplets produced to be in the range from sub-micron dimensions (between about 1 micron and 100 nm) to nanoscale dimensions (below about 100 nm).

Interfacial Tension Measurements.

We measure the interfacial tensions between each of the three immiscible oils and an aqueous SDS solution at $C_{SDS}$=5 mM using a duNouy ring surface tensiometer. For the PFPMS oil, fluorinated MASURF surfactant at 0.3% is also present in addition to SDS. The measured values are: $\sigma_{W-O1}$=14.1 dyn/cm (W-PPPMS), $\sigma_{W-O2}$=12.7 dyn/cm (W-POMS), and $\sigma_{W-O3}$=12.0 dyn/cm (W-PFPMS); uncertainties for these measured values are ±0.2 dyn/cm. To measure the oil-oil interfacial tensions, we employ a non-wetting resting droplet method. We image steady-state shapes of millimeter-scale gravitationally deformed droplets in profile as they rest on a level flat surface without wetting it while being fully surrounded by a different immiscible oil. For all three combinations of oil pairs, the deformed droplet shape is well approximated by truncated oblate spheroid. Knowing the mass density differences between the oils, we deduce the interfacial tension based on changes in the gravitational potential energy and the interfacial energy, proportional to the interfacial area of the deformed droplet, relative to an undeformed sphere. Numerical integration using the measured profile shapes of deformed droplets yields: $\sigma_{O1-O2}$=2.9±0.4 dyn/cm (PPPMS-POMS), $\sigma_{O1-O3}$=15.4±1.5 dyn/cm (PPPMS-PFPMS), and $\sigma_{O2-O3}$=21.0±2.1 dyn/cm (POMS-PFPMS).

Example 2: Self-Limiting Droplet Fusion in Ionic Emulsions

In this example embodiment, Self-limiting droplet coalescence is induced by mixing an anionically stabilized oil-in-water emulsion with a cationic surfactant solution. If two or more mutually immiscible oils are used, anisotropic droplets having structured internal oil-oil interfaces form.

We make an oil-in-water emulsion, which is initially stabilized using a first ionic surfactant, and mix it with a solution of a second ionic surfactant having the opposite charge, thereby inducing massively parallel droplet fusion. A transient disruption of the screened charge repulsive barrier between interacting droplets, caused by the second ionic surfactant, arises from significant yet temporary charge neutralization of the first ionic surfactant on the surfaces of the oil droplets while mixing occurs. Interestingly, if a moderate molar excess of one surfactant exists, then the resulting emulsion re-stabilizes after limited droplet fusion. By adjusting the droplet volume fraction, concentrations of first and second surfactants, and volumes of the emulsion and the solution of the second surfactant, we control the degree of droplet coalescence and achieve a self-limiting droplet fusion process. Using optical microscopy we observe that flat, thin, crystalline films can form between the two oil compartments after fusion of two or more immiscible microscale droplets. However, no such crystalline films are seen on the highly curved oil-oil interfaces inside nanoscale droplets, composed of two or more immiscible oils fused in the same manner, as revealed by cryogenic transmission electron microscopy.

Here, we explore combining an anionically stabilized O/W emulsion with an appropriately selected cationic surfactant solution to cause a self-limiting, massively parallel, controllable form of droplet fusion. Initially, when a sufficiently concentrated cationic solution is rapidly mixed with an anionically stabilized emulsion, droplet fusion occurs. However, for a certain range of molar ratios of anionic to cationic surfactant, this transient process of droplet fusion ceases and the emulsion re-stabilizes, yielding a self-limiting coalescence reaction. For a simple O/W emulsion, all oil droplets have the same oil type and are therefore miscible, so droplet fusion is equivalent to coalescence. We cause droplet coalescence of a microscale monodisperse O/W emulsion by this self-limiting process, and we measure resulting droplet size distributions using optical microscopy. For certain molar ratios of anionic-to-cationic surfactant (e.g. when an excess of anionic surfactant is present), we observe discrete peaks in the droplet size distributions at larger sizes, corresponding to the fusion of integral numbers of droplets without macroscopic oil breakout prior to droplet re-stabilization by the excess surfactant.

We extend this approach to mixed emulsions containing droplets of two or more types of mutually immiscible oils and produce anisotropic fused droplets having overall dimensions ranging from the microscale to the nanoscale. When this self-limiting droplet fusion process is applied to a mixed emulsion of this type, we form stable emulsions of compartmentalized droplets that have structured internal oil-oil interfaces. Depending on the conditions, the resulting droplets can be Janus (binary),[12,13, 49] Cerberus (ternary), or even higher-order. Using high-speed optical video microscopy, we have captured a droplet-droplet fusion event and report the kinetics of the increase in area of contact between fusing droplets. Interestingly, for microscale droplets, we observe evidence that solid thin films containing crystallized surfactant can exist between fused immiscible oil droplets; whereas, we do not observe such solid films for multi-compartment nanoscale droplets at the same conditions, based on cryogenic transmission electron microscopy (cryo-TEM) images of the highly curved internal oil-oil interfaces.

To explain these results, we hypothesize that self-limiting droplet fusion occurs when the stabilizing screened-charge repulsive barrier energy between droplet interfaces is temporarily lowered to values near or below thermal energy $k_BT$ through a non-equilibrium process of transient localized interfacial neutralization involving attractive interactions between oppositely charged surfactants. If an adequate molar excess of stabilizing surfactant remains after mixing, then re-equilibration and re-distribution of the excess charge on the droplets' interfaces subsequently increases the repulsive barrier above $k_BT$, and droplet fusion ceases. Thus, the transient droplet fusion reaction can be regulated to be either self-limiting or not, depending on the relative molar amounts of the two oppositely charged surfactants. The hydrophobic tails of the charged surfactant molecules facilitate and enhance interfacial consequences of charge neutralization, such as droplet fusion, as compared to simple ionic salts that are not amphiphilic.

Experimental

Materials

The salt cetyltrimethylammonium bromide (CTAB) is dissolved in deionized water; this is referred to as the solution of the cationic surfactant. CTAB has a molecular weight of $M_{W,CTAB}$=364.5 g/mol and has a critical micelle concentration of $CMC_{CTAB}$=0.9 mM.[4] Sodium dodecyl sulfate (SDS) is the anionic surfactant ($M_{W,SDS}$=288.4 g/mol and $CMC_{SDS}$=8 mM). If fluorinated oil is used as the dispersed phase, an anionic fluorinated surfactant solution (Masurf FS-615) is also added at ≈0.1% v/v to the emulsion (i.e. prior to inducing destabilization by mixing with CTAB) to confer additional stability against droplet coalescence. All surfactant solutions and emulsions are made using water deionized by a Millipore Milli-Q system.

Soybean oil (mass density $\rho_{soy}$≈0.92 g/mL) is used in monodisperse O/W emulsions for experiments on droplet coalescence involving only a single oil type. For different self-limiting fusion experiments involving droplets of mutually immiscible oils, we use: (1) soybean oil and 10 cSt PDMS silicone oil, $\rho_{PDMS}$=0.935 g/mL, $M_{W,PDMS}$≈1250 g/mol; (2) poly-(3,3,3-trifluoropropylmethylsiloxane) (PFPMS, $\rho_{PFPMS}$=1.28 g/mL, $M_{W,PFPMS}$≈4600 g/mol) and poly-((2-phenylpropyl)methylsiloxane) (PPPMS, $\rho_{PPPMS}$=1.02 g/mL); (3) PFPMS and squalene ($\rho_{squalene}$=0.86 g/mL, $M_{W,squalene}$≈410.7 g/mol); and (4) poly-(octylmethylsiloxane) (POMS, $\rho_{POMS}$=0.91 g/mL), PPPMS, and PFPMS. All silicone oils are obtained from Gelest. In some experiments, to differentiate between soybean oil and PDMS droplets, pyrene, a blue-fluorescing fluorophore, is added at 50 mM in soybean oil before emulsification. We have also made O/W emulsions of droplets containing ghee, a form of clarified butter fat in which water and other milk solids, such as proteins, have been removed.

Self-Limiting Droplet Coalescence: Single Oil Type

Using a microfluidic droplet junction chip (Dolomite Microfluidics, nearly square 100 μm×105 μm channel cross-section), we create two monodisperse soybean-SDS O/W master emulsions: a first master emulsion for a set of measurements at constant droplet volume fraction and a second master emulsion for a set of measurements at constant surfactant mole fraction mixing ratio. Both master soybean oil-SDS O/W emulsions have an average droplet diameter $d_o \approx 85$ μm. The droplets are initially dispersed in an aqueous SDS solution at a concentration $C_{SDS}=50$ mM. Subsequently, we reduce $C_{SDS}$ by allowing the emulsion to cream, removing the continuous phase below the cream, diluting the remaining cream with an aqueous solution having lower $C_{SDS}$, and repeating until $C_{SDS}=5$ mM, below $CMC_{SDS}$. Using optical microscopy, we determine the number-weighted size distribution of the soybean O/W master emulsions via digital image analysis of at least 200 droplets. The master emulsions are highly monodisperse; the polydispersity, defined by $\delta a/<a>$, where $\delta a$ is the standard deviation and $<a>=d_o/2$ is the average radius of the droplet size distribution, of both master emulsions is $\delta a/<a> \approx 0.04$.

Figures 8A, 8B:
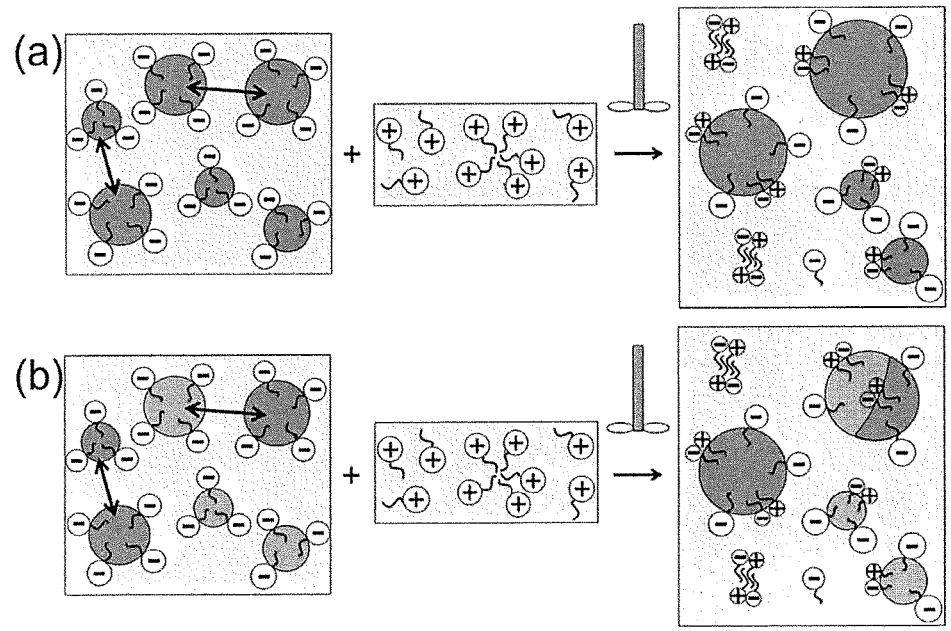
FIGS. 8A-8B show the reaction schematics of self-limiting droplet coalescence and fusion in ionic emulsions caused by disruption of charge stabilization by oppositely charged amphiphiles.

In a first set of experiments, we investigate changes in the droplet size distribution caused by self-limiting coalescence at fixed mole fraction of anionic SDS surfactant as a function of the droplet volume fraction. Through a combination of gravitational creaming and continuous phase removal, the first master monodisperse soybean O/W emulsion is concentrated to $\phi=0.43$. This concentrated emulsion is diluted to the desired $\phi$ for fusion by adding 5 mM SDS solution. We define the final SDS surfactant mole fraction (after mixing) to be: $\chi_{SDS}=n_{SDS}/(n_{SDS}+n_{CTAB})$, where $n_{SDS}$ is the number of moles of SDS in the emulsion prior to mixing and $n_{CTAB}$ is the number of moles of cationic CTAB in the surfactant solution prior to mixing. Thus, the CTAB mole fraction is $\chi_{CTAB}=1-\chi_{SDS}$. To fuse droplets, we rapidly mix 30 μL of a 5 mM CTAB solution with 70 μL of the emulsion having a desired $\phi$, thereby fixing $\chi_{SDS}$ at 0.7. The mixture is shaken continuously for about 3 seconds. We choose $\chi_{SDS}=0.7$ in order to create significant droplet fusion in a self-limiting reaction while minimizing surfactant crystallite formation and uncontrolled fusion leading to macroscopic oil phase separation (i.e. "oil breakout"). A schematic of this process is shown in FIG. 8A.

In a second set of experiments, we vary $\chi_{SDS}$. Again, using gravitational creaming and continuous phase removal, the second master emulsion is first set to $\phi=0.078$ and $C_{SDS}=5$ mM. To create fusion at a desired $\chi_{SDS}$, we mix 100 μL×$\chi_{SDS}$ of emulsion with 100 μL×(1-$\chi_{SDS}$) of CTAB solution at 5 mM, yielding a total mixture volume of 100 μL. This also changes $\phi$ a minor amount; for instance, $\phi$ is reduced to 0.047 at $\chi_{SDS}=0.6$. Since the average center-to-center separation between droplets scales as $\phi^{-1/3}$, this small change in $\phi$ created by the mixing procedure results in only about a 15% change in interdroplet separation for this set of experiments, and the dominant coalescence effects result mostly from changes in $\chi_{SDS}$.

In experiments involving either master emulsion, we wait three minutes after mixing, longer than the time required for re-stabilization of droplets in the self-limiting reaction, and then deposit about 5 μL of the resulting emulsion on a microscope slide. To dilute the droplets for clarity of imaging and to inhibit any further fusion, excess 5 mM SDS is added to the deposited emulsion, the slide is sealed, and the number-weighted size distribution is measured using optical video microscopy. We ignore any small aggregates of complexed surfactant crystallites that may have formed in the continuous phase outside the droplets.

Self-Limiting Droplet Fusion: Two or More Types of Mutually Immiscible Oils

To create multi-component microscale emulsion droplets, a Fisher Scientific PowerGen 125 rotary mixer is initially used to create a set of separate O/W microscale emulsions of $N_O$ types of mutually immiscible oils, such that each emulsion has the same initial desired $\phi_i$ and $C_{SDS}=5$ mM. Equal volumes of each emulsion are mixed together, yielding a stable "mixed emulsion" containing a combination of immiscible oil droplets having different oil types. Thus, the final total oil volume fraction $\phi_T$ of the mixed emulsion is the same as $\phi_i$, but the final volume fractions of individual oil types are reduced by $1/N_O$. To fuse the mixed emulsion having $\phi_i$ at a desired $\chi_{SDS}$, we combine 100 μL×$\chi_{SDS}$ of the mixed emulsion with 100 μL×(1-$\chi_{SDS}$) of CTAB solution at 5 mM, yielding a total volume of 100 μL. A schematic of this process is shown in FIG. 8B. After waiting three minutes, 5 μL of the resulting emulsion is placed on a microscope slide and diluted with 5 mM SDS. Next, the slide is sealed and an optical microscope is used to probe the fused emulsion system.

FIGS. 8A-8B show the reaction schematics of self-limiting droplet coalescence and fusion in ionic emulsions caused by disruption of charge stabilization by oppositely charged amphiphiles. FIG. 8A shows an Anionically stabilized oil-in-water emulsion containing a single oil type and a cationic surfactant solution are mixed together to cause self-limiting coalescence between miscible droplets. Depending upon the surfactant concentrations and types, cationic-anionic surfactant complexes (e.g. micelles and crystallites) can form. Figure b shows an anionically stabilized mixed emulsion containing two different immiscible oil types and a cationic surfactant solution are mixed together. Self-limiting droplet fusion merges droplets of the same oil types and also forms complex compartmentalized droplets (e.g. Janus droplet—upper right) that contain both immiscible oils. Symbols: continuous aqueous phase is represented by area surrounding each of the droplets; positively and negatively charged heads with tails represent cationic and anionic surfactants, respectively; oil type 1 (darker gray); oil type 2 (lighter gray). Neutralized multi-molecular surfactant structures are shown without white backgrounds for head groups. Spectator counter-ions that maintain charge neutrality are omitted for clarity.

In addition, we fabricate nanoscale O/W emulsions, which can be used in subsequent surfactant-induced fusion experiments to create complex multi-oil nanodroplets, as follows. We initially create individual O/W microscale emulsions using $N_O$ types of mutually immiscible oils as before; each emulsion contains droplets of a single oil type yet the same desired $\phi_i$ and is stabilized by SDS at $C_{SDS}=5$ mM. Each of the individual microscale emulsions is subjected to high-flow rupturing using a high-pressure microfluidic homogenizer; we pass each emulsion through a total of N=6 times at a liquid pressure of $p_1 \approx 18,000$ psi, yielding several individual O/W nanoemulsions,[25] each having a single oil type. Next, equal volumes of each nanoemulsion are mixed together, yielding a stable mixed nanoemulsion containing immiscible oil droplets having different oil types but sharing the same common anionic surfactant, SDS. We induce self-limiting fusion of droplets in the mixed nanoemulsion by combining it with a CTAB surfactant solution having the opposite charge at the desired $\chi_{SDS}$.

To make an emulsion of solidified ghee, we melt solid ghee by heating it to 50° C. and emulsify it while hot into a 5 mM aqueous SDS solution, also preheated to 50° C., using a PowerGen 125 homogenizer at $\phi=0.02$. As the resulting microscale emulsion cools to room temperature, the ghee droplets solidify. This dispersion of solidified ghee droplets is then mixed at equal volumes with a microscale 5 mM SDS-stabilized PDMS O/W emulsion before fusing at $\chi_{SDS}=0.7$ using a 5 mM CTAB solution as previously described for liquid microscale droplets.

While we focus on creating droplet fusion by combining an ionic mixed immiscible-oil emulsion with an oppositely charged surfactant solution, we have also made structured multi-oil component droplets through self-limiting droplet fusion by mixing two separate O/W emulsions of immiscible oils stabilized by oppositely charged surfactants. For example, we make a first microscale soybean oil-in-water emulsion at $\phi=0.2$ stabilized by anionic SDS at $C_{SDS}=5$ mM and a second microscale PDMS oil-in-water emulsion at $\phi=0.2$ stabilized by cationic CTAB at $C_{CTAB}=5$ mM. We rapidly mix 70 µL of the first soybean O/W emulsion with 30 µL of the second PDMS O/W emulsion, thereby setting $\chi_{SDS}=0.7$ and creating a self-limiting droplet reaction. The resulting emulsion re-stabilizes after a limited degree of droplet fusion, thereby producing a significant population of fused Janus droplets that contain separate internal compartments of soybean oil and PDMS sharing a common internal oil-oil interface. Likewise, although we have focused on representative examples of mixtures of cationic CTAB solutions with SDS-stabilized anionic emulsions, we have also produced self-limiting droplet fusion reactions, which also produce Janus and Cerberus droplets, by mixing anionic SDS solutions with CTAB-stabilized cationic emulsions.

Microscopic Imaging

To perform brightfield optical microscopy on microscale emulsions, we use a Nikon TE2000 inverted microscope equipped with 20×, 40×, and 60× objectives, a 1.5× slider, and a digital CCD camera (Point Grey Flea2). To perform fluorescence microscopy, we use mercury lamp illumination and a UV-2A Nikon filter cube set. This set allows soybean oil emulsion droplets doped with pyrene to fluoresce and appear blue. Micrograph backgrounds outside of the droplet boundaries are Gaussian-blurred to emphasize features in the droplets of interest.

For temperature-controlled optical microscopy, the microscope is equipped with a temperature-controlled stage. A sample containing fused droplets is initially placed in a microscope slide, sealed, and observed at T≈25° C. A micro-Temperature Controller (mTCII) then heats the stage to T≈50° C. based on feedback from a thermocouple placed on the cover glass. The sample is then returned to T≈25° C. Micrographs are taken after holding for at least 20 minutes at each temperature extreme.

To manipulate droplet placement and orientation of multicomponent droplets, a single-beam optical trap is used. A linearly polarized 15 mW HeNe laser beam is expanded by a factor of about 5 (i.e. to ≈1 cm diameter beam-waist) and passed into the back of a 1.4 NA 60× objective. To prevent imaging of the laser light, a laser-line rejection filter is placed in front of the camera.

To obtain time-resolved microscopy images of microscale droplet fusion, a slightly different procedure is used. A small volume of the combined immiscible-oil emulsion is first placed on a glass microscope slide having no coverslip. An appropriate volume of the CTAB solution, ensuring $\chi_{SDS}=0.7$, is then placed next to the emulsion such that the two solutions barely touch. Diffusion of the CTAB solution into the emulsion induces droplet fusion, which we capture using a high-speed digital CMOS camera (Silicon Imaging SI-1280 FM-CL). Image backgrounds have been Gaussian-blurred to remove structures beyond the droplet interfaces of interest.

Real-space images of nanoscale droplets are obtained by cryo-TEM. We ensure the ice outside the droplets is vitreous; inclusion artifacts within droplets are not observed.[30] After loading and blotting the grids, which support thin films of dilute nanoemulsions, we rapidly freeze the grids by gravity quenching them into liquid ethane. Grids are then transferred to an FEI Tecnai G$^2$ TF 20 TEM and imaged in low-dose mode at 200 kV.[30] Levels and contrast in cryo-TEM images have been digitally adjusted to make key features, such as oil-oil interfaces, more apparent.

Optical Transmission Measurements

Optical transmission measurements are performed at a wavelength of $\lambda=600$ nm through a 1 cm path-length quartz cell using a Hewlett-Packard HP 8453 diode-array UV/Vis spectrophotometer having Peltier temperature control. The transmission, $\tau(T)$, of a $\chi_{SDS}=0.7$ surfactant-only mixture is followed as the mixture is heated from 25° C. to 70° C. at ≈0.2° C./min.

Results and Discussion

Self-Limiting Droplet Coalescence: Single Oil Type

In a first systematic study, we examine the dependence of coalescence on $\phi$ for a fixed $\chi_{SDS}=0.7$. At this $\chi_{SDS}$ an appreciable amount of coalescence can occur without any observable macroscopic phase separation over a wide range of $\phi$. The normalized probability distribution, p, of finding a given dimensionless diameter ratio $d/d_o$ in the resulting emulsion at a specific $\phi$ is plotted in FIG. 9A. The volume fraction at $\phi=0$ represents the initial monodisperse emulsion. For other non-zero $\phi$, distinct peaks are easily resolved; these peaks in p occur at $d/d_o=N^{1/3}$, corresponding to the fusion of an integral number N of monodisperse droplets. Thus, we observe sharp resolvable peaks at $d/d_o\approx1.26$, 1.44, 1.59, and 1.71, corresponding to the fusion of 2, 3, 4, and 5 droplets, respectively. For dilute $\phi$, the area under each successive peak decreases, so the probability of N droplets having fused as a result of adding the cationic surfactant prior to re-stabilization becomes less likely for larger N. As $\phi$ increases, the area under the peak at $d/d_o=1$ decreases, whereas the areas under the peaks for $d/d_o>1$ increase, indicating that more droplet coalescence occurs when $\phi$ is larger. At $\phi=0.4$, macroscopic phase separation of the soybean oil is seen; however, a dilute emulsion having reduced $\phi$ still remains underneath the phase-separated oil layer. The analysis of this lower dilute emulsion is shown in FIG. 9A (* curve).

In a second set of systematic studies, we have also examined the effect of $\chi_{SDS}$ on coalescence at $\phi=0.078$ before fusing (see Methods). We have chosen this particular $\phi$ because significant droplet coalescence can occur over a wide range of $\chi_{SDS}$ without any obvious macroscopic oil breakout. The normalized probability distributions p as a function of $d/d_o$ at a specific $\chi_{SDS}$ are plotted in FIG. 9B. The curve at $\chi_{SDS}=1$ represents the initial monodisperse emulsion without any added CTAB solution. Again, we observe a set of sharp peaks in $p(d/d_o)$ as a consequence of the discrete nature of the number of droplet coalesce events before the emulsion re-stabilizes in the self-limiting reaction process. Very little coalescence is observed at $\chi_{SDS}=0.8$ and 0.9; only a very small secondary peak is observed at $d/d_o\approx1.26$. However, significant yet controlled coalescence is observed at $\chi_{SDS}=0.7$, and many peaks are clearly visible. The degree of coalescence increases as additional CTAB solution is added. At $\chi_{SDS}$=0.6, oil breakout appears at the top of the mixture; however, a dilute emulsion having reduced ϕ still remains underneath the phase-separated oil layer. The analysis of the lower dilute emulsion is shown in FIG. 9B (* curve).

Figures 9A, 9B:
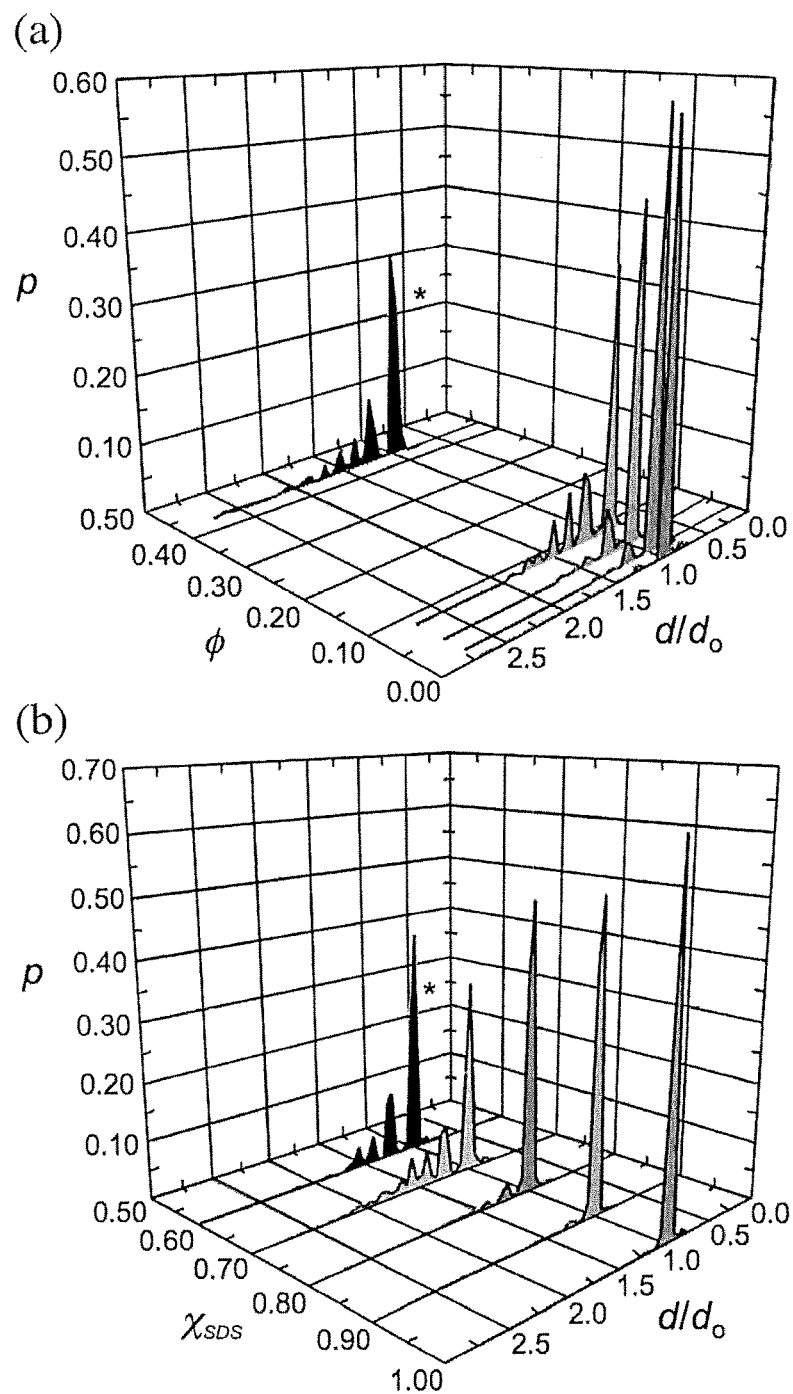
FIGS. 9A-9B show graphs plotting the normalized probability distribution, p, of finding a given dimensionless diameter ratio $d/d_o$ in the resulting emulsion at a specific $\phi$ and $\chi_{SDS}$.

FIG. 9A shows the number-weighted normalized probability distribution p as a function of the dimensionless diameter ratio $d/d_o$ at volume fractions ϕ=0, 0.017, 0.043, 0.082, and 0.43 after self-limiting coalescence of a $C_{SDS}$=5 mM soybean oil emulsion induced by mixing with $C_{CTAB}$=5 mM surfactant solution at constant SDS mole fraction $\chi_{SDS}=n_{SDS}/(n_{SDS}+n_{CTAB})$=0.7. The initial droplet size distribution is shown at ϕ=0. The star * at ϕ=0.43 indicates that macroscopic phase separation of oil occurred; the reported $p(d/d_o)$ for * does not account for oil breakout: actual normalized peak heights in * would be much smaller than those shown. FIG. 9B shows $p(d/d_o)$ at $\chi_{SDS}$=0.60, 0.70, 0.80, 0.90, and 1 after self-limiting coalescence of a $C_{SDS}$=5 mM soybean oil emulsion induced by mixing with $C_{CTAB}$=5 mM at an initial ϕ=0.078. The initial size distribution is shown at $\chi_{SDS}$=1. The star * at $\chi_{SDS}$=0.60 indicates oil breakout; the reported p values are only relative and would be much smaller than shown if macroscopic oil breakout had been taken into account in the normalization.

We hypothesize that the self-limiting coalescence reaction proceeds as follows. When the CTAB is rapidly mixed with the SDS-stabilized O/W emulsion, CTAB molecules complex with SDS molecules to form charge-neutral structures. Some charge-neutral structures are formed in solution; these include structures ranging from a single neutral complex of one SDS molecule and one CTAB molecule to larger scale crystallites that contain SDS and CTAB. In addition, simultaneously, on the interfaces of the droplets, CTAB molecules adsorb and complex with SDS molecules that have been providing the stabilizing charge repulsion between interfaces of droplets that may encounter each other as they diffuse. The transient disruption of the local surface charge density on the interfaces of the droplets, caused by the CTAB molecules, leads to a reduction in the repulsive barrier, so that it becomes comparable to or less than $k_BT$, enabling thermal forces to drive droplet fusion. Although we mix rapidly to homogenize the surfactant concentrations and then allow diffusion to drive droplet fusion, it is possible that applied convective forces during mixing could influence the degree of the resulting droplet fusion. Especially for nanoscale droplets, it is likely that most of the droplet fusion is diffusion-driven. For $\chi_{SDS}$=0.5, there is one CTAB molecule for every SDS molecule; in this case, the neutralization of the charge is complete, oil breakout occurs, and the emulsion is destabilized. For $\chi_{SDS}$ that is only slightly below unity, only a small number of CTAB molecules relative to SDS molecules are added to the emulsion, and adequate excess SDS remains in the emulsion during complexing and neutralization to maintain droplet stability.

However, for intermediate values of $\chi_{SDS}$ between 0.5 and 1, such as $\chi_{SDS}$=0.7, the droplet fusion process is more complex and can be self-limiting. Interestingly, the destabilization of the droplet interfaces by complexing and neutralization of the oppositely charged surfactants is only transient. As the CTAB solution is mixed into the SDS-stabilized O/W emulsion, gradients in surfactant concentrations and therefore variations in local $\chi_{SDS}$, temporarily reduce the interfacial repulsive barrier heights between droplet interfaces, some of which become comparable to or less than $k_BT$. During this transient of localized quasi-neutralization of droplet interfaces, some droplet fusion occurs, but ultimately enough un-neutralized charged surfactant remains to re-populate the droplet interfaces and restore the interfacial repulsive barrier heights to values that are much larger than $k_BT$. It is also possible that some excess SDS adsorbs onto SDS-CTAB crystals that may also have formed, providing repulsions between crystals and other crystals or between crystals and droplets. In principle, droplet fusion caused by solid surfactant crystals bridging between droplets could be an additional destabilization mechanism, but this mechanism is unlikely to be a primary source of fusion, since we have observed that such crystals can co-exist with microscale emulsion droplets without causing coalescence using optical microscopy.

During the transient destabilization, the degree of droplet fusion depends on the probability of droplets undergoing one or more collisions. Since the rate of droplet collisions increases as the droplet volume fraction is raised, this model is consistent with our observations of a higher degree of droplet fusion as ϕ is increased at fixed $\chi_{SDS}$=0.7. Re-stabilization of the emulsion occurs because excess SDS in the continuous phase diffuses and adsorbs onto the droplet interfaces, thereby increasing the interfacial charge density to an adequate level to raise the repulsive barrier well in excess of $k_BT$. It is also possible that densely structured SDS-CTAB complexes (e.g. a liquid crystalline or even a crystalline film) can form at the droplet interfaces, anchored there by many hydrophobic tails; such solid films of complexed surfactant could also stabilize droplets against coalescence.

Self-Limiting Droplet Fusion: Two or More Types of Mutually Immiscible Oils

Figures 10A, 10B, 10C, 10D:
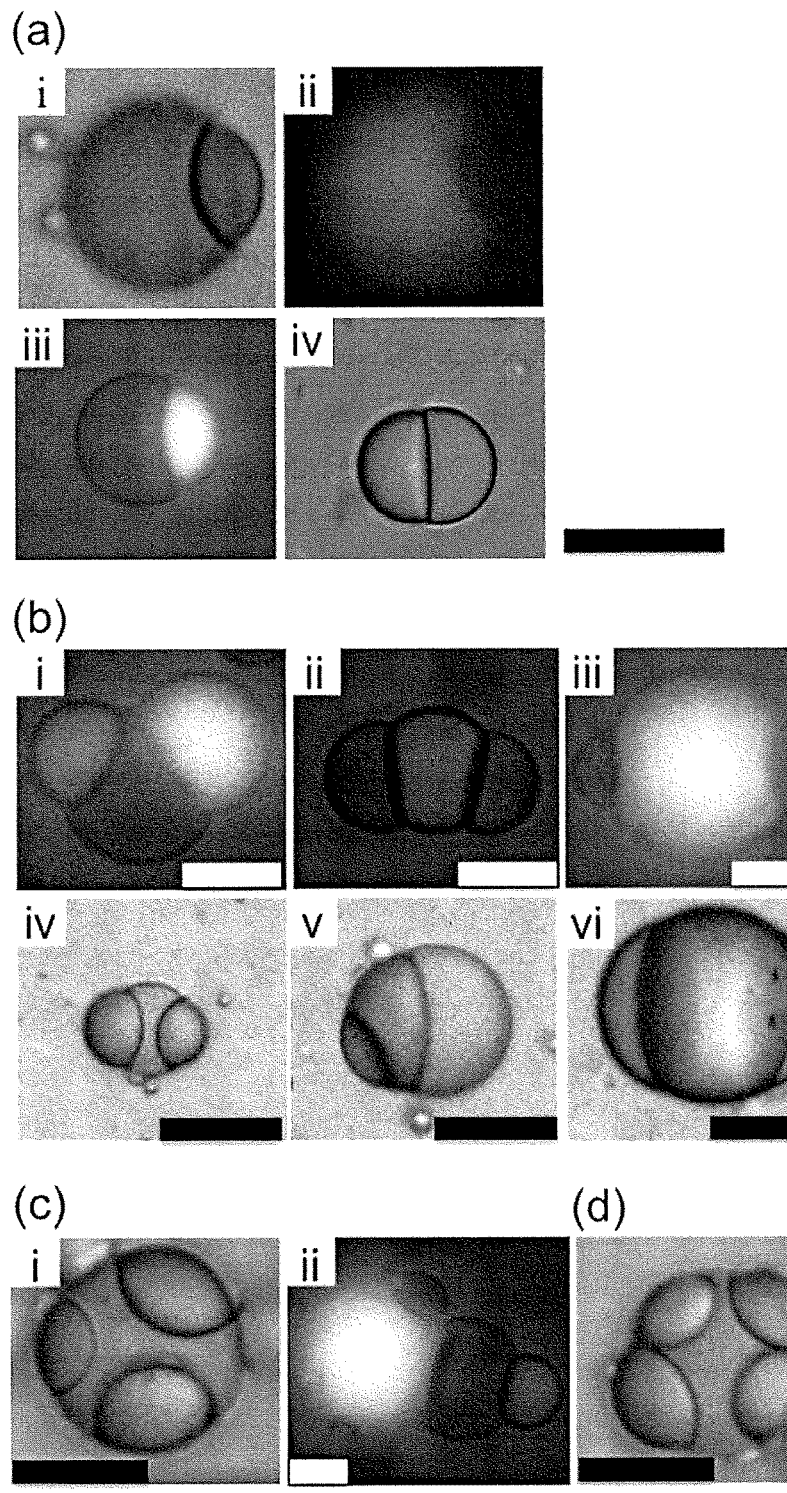
FIGS. 10A-10D show optical microscopy observations of re-stabilized compound droplet structures after fusion that have been formed by mixing equal volumes of a $C_{SDS}$=5 mM, $\phi_T$=0.2 soybean oil emulsion droplets+PDMS oil emulsion droplets with a CTAB solution $C_{CTAB}$=5 mM at $\chi_{SDS}$=0.7.

We make a mixed (O1,O2)/W emulsion composed of droplets of soybean oil [(oil 1, designated O1) and droplets of PDMS (oil 2, designated O2)] stabilized by SDS, and we rapidly mix this mixed (O1,O2)/W emulsion with a CTAB solution at $\chi_{SDS}$=0.7 (see Methods). Optical micrographs of the resulting microscale Janus droplets, composed of one soybean oil droplet and one PDMS droplet that have fused together, as a result of transient interfacial destabilization caused by the CTAB, are shown in FIG. 10A. A Janus droplet under ultraviolet illumination exhibits pyrene fluorescence from the soybean oil in the larger convex-concave lens (FIG. 10A—panel ii); for comparison, the same droplet under normal brightfield illumination is also shown (FIG. 10A—panel i). By contrast, although the droplet has a similar shape, the small biconvex lens is composed of soybean oil (FIG. 10A—panel iii). Not all droplets have such a curved appearance of an internal O1-O2 interface. In some cases, the O1-O2 interfaces are actually flat, possibly arising from both O1 and O2 wetting a flat, thin SDS-CTAB surfactant crystalline film. An example of a Janus droplet having a flat interface is also shown (FIG. 10A—panel iv). The micrographs of FIG. 10B show Cerberus droplets resulting from the fusion of three oil droplets. Since only two immiscible oils are used in the composition, the central droplet in a linear Cerberus fused-droplet morphology must be a different type of oil than that of the end droplets: either O1-O2-O1 (FIG. 10B—panel i) or O2-O1-O2 (FIG. 10B—panels ii, iii). End droplets may fuse to create different angular orientations with respect to the center droplet; the fused droplet structure appears to be rigid and end droplets do not diffuse over the surface of the central droplet when viewed microscopically. For example, in FIG. 10B—panel i, if two different line segments are drawn from the center of the central droplet through the centers of the two end droplets, then these line segments would be separated by approximately 120°. However, FIG. 10B—panel iii, these two line segments would be separated by about 180°. In both FIGS. 9A and 9B, widely different internal O1-O2 interfacial curvatures can be observed when considering the entire ensemble of fused droplets that have formed. For three-droplet Cerberus structures in FIG. 10B, we observe that the two end droplets can have oil-oil interfacial structures that appear: concave-concave (panel iv), concave-convex (panel v), and convex-convex (panel vi).

FIGS. 10A-10d show optical microscopy observations of re-stabilized compound droplet structures after fusion that have been formed by mixing equal volumes of a $C_{SDS}$=5 mM, $\phi_T$=0.2 soybean oil emulsion droplets+PDMS oil emulsion droplets with a CTAB solution $C_{CTAB}$=5 mM at $\chi_{SDS}$=0.7. FIG. 10A shows Janus (two-fused) droplets; soybean oil containing pyrene fluoresces (light gray region in panel ii and brighter region in panel iii), enabling the two oils to be differentiated. Scale bar: 20 µm. FIG. 10 b shows Cerberus (three-fused) droplets created with pyrene (panels i-iii: brighter droplet regions) and without pyrene (panels iv-vi) in soybean oil. FIG. 10C shows four fused droplets: (i) without pyrene and (ii) with pyrene in soybean oil. FIG. 10D shows five fused droplets. Scale bars in (b-d) are 10 µm.

Beyond Janus and Cerberus structures, which are more frequently found, we also observe more complex resulting structures of four or more distinguishable droplets. For instance, three droplets of one oil type may fuse with a single central droplet of the other immiscible oil type (FIG. 10C, panel i); these three peripheral droplets remain separated and do not touch. Alternatively, a linear chain of four droplets may be formed if the immiscible oil types alternate (e.g. O1-O2-O1-O2) (FIG. 10C, panel ii). In this case, thermal energy is unable to overcome interfacial energies to cause the rearrangement of the droplets into configurations that would enable coalescence of droplets having the same oil types. An example of a five-component droplet is shown in FIG. 10D. Other infrequently observed, yet stable, compound droplet morphologies include an alternating linear chain of five droplets (O1-O2-O1-O2-O1) and a branched isomeric alternating linear chain.

Time-Resolved Fusion of Microscale Droplets

Figures 11A, 11B, 11C:
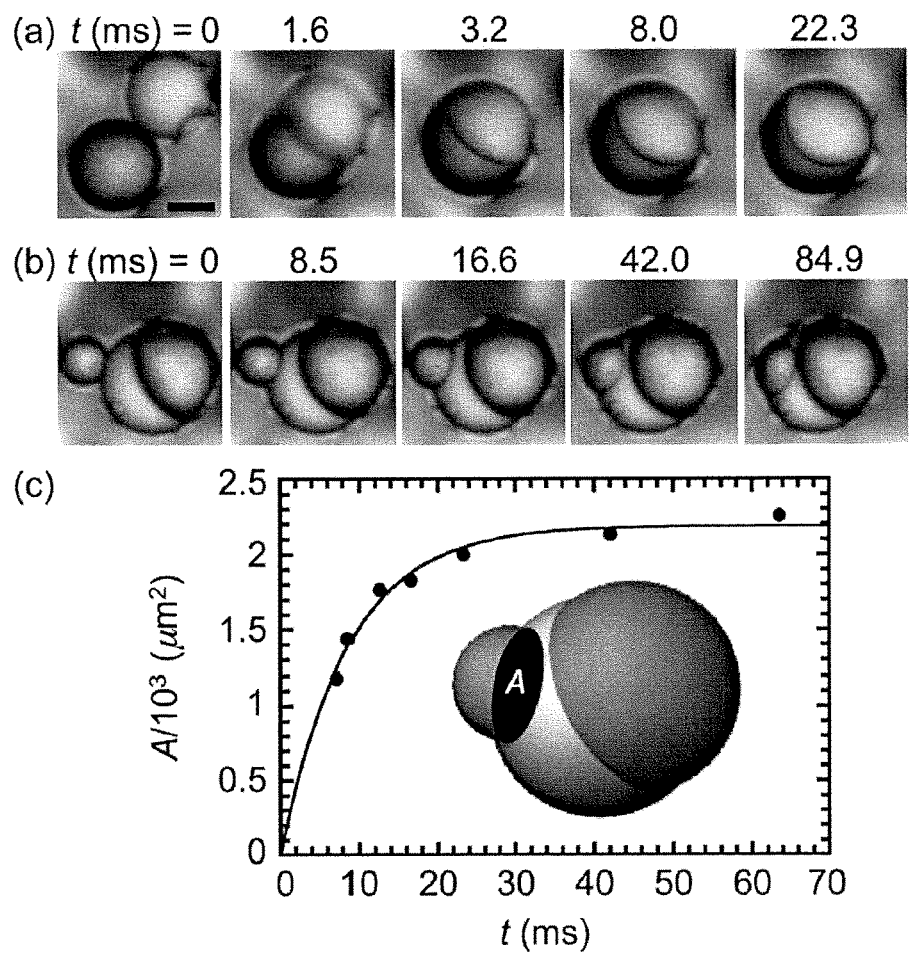
FIGS. 11A-11C show high-speed optical video microscopy observation of time-resolved fusion of droplets in a mixed emulsion of soybean oil and PDMS: $C_{SDS}$=5 mM, $\phi_T$=0.05 emulsion is mixed with $C_{CTAB}$=5 mM solution at $\chi_{SDS}$=0.7.

Results of high-speed optical video microscopy of soybean oil droplets fusing with PDMS droplets are shown in FIGS. 11A-11c. In FIG. 11A, a soybean oil droplet fuses with a PDMS droplet to form a Janus droplet. As fusion occurs, the compound droplet also rotates as a result of density differences between the two immiscible oils. Both droplet-droplet adhesion and this rotation lead to an increase in the curvature of the oil-oil interface. In FIG. 11B, a third droplet fuses with a Janus droplet to become a Cerberus droplet.

FIGS. 11A-11C show high-speed optical video microscopy observation of time-resolved fusion of droplets in a mixed emulsion of soybean oil and PDMS: $C_{SDS}$=5 mM, $\phi_T$=0.05 emulsion is mixed with $C_{CTAB}$=5 mM solution at $\chi_{SDS}$=0.7. FIG. 11A shows a soybean oil droplet fuses with a PDMS droplet. FIG. 11B shows a Janus droplet fuses with another droplet to become a Cerberus droplet. FIG. 11C shows an estimated contact area, A, between the fusing droplets in (b) as a function of time, t. Solid curve is a fit to an exponential form. Inset highlights the defined circular contact area, A, which appears as an ellipse due to the droplet orientation. Scale bar is 42 µm and applies to all micrographs.

An estimated contact area, A, between the fusing droplets of FIG. 11B is plotted as a function of time in FIG. 11C. We assume that A can be estimated by the area of a disk, which is rotated relative to the viewing direction, causing it to appear elliptical as imaged. To estimate A, we measure the maximal spatial dimension of the black region and use this as the diameter of the disk. We empirically fit the measured area to an exponential form: $A(t)=A_f[1-\exp(-t/t_o)]$ $A(t)=A_f(1-b\exp(-t/t_o))$, where $A_f$ is the final interfacial area shared between the two fused droplets and $t_o$ is a time scale characterizing the droplet fusion kinetics. From the fit, which reasonably describes the data, we find $A_f=(2.2\pm0.05)\times 10^3$ µm² and $t_o=8.5\pm0.6$ ms.

Figures 12A, 12B, 12C:
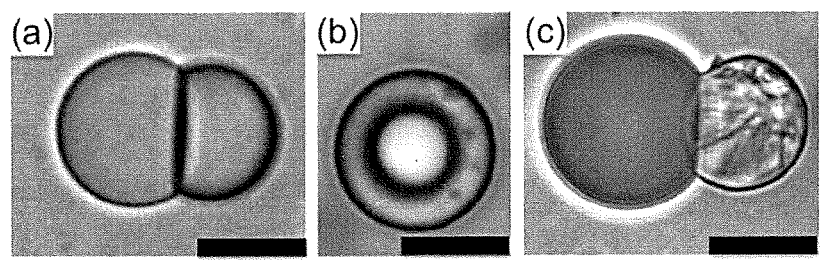
FIGS. 12A-12C show optical micrographs of Janus droplet structures after inducing fusion.

Combinations of dispersed-phase materials other than soybean oil and PDMS may also be used to form multi-droplet structures by surfactant-induced fusion. Liquid-liquid examples include PFPMS/PPPMS (FIG. 12A) and PFPMS/squalene (FIG. 12B). Hybrid solid-liquid Janus structures may also be formed by fusing a dispersion of solid ghee particles with PDMS emulsion droplets at room temperature (FIG. 12C). The relative densities of the immiscible phases within fused droplets dictate whether or not a non-engulfed linear structure can be readily seen. If both O1 and O2 have mass densities less than or greater than the density of the aqueous continuous phase, $\rho_c$, then the axis of a Janus droplet is usually not perpendicular to the focal plane and a non-engulfed linear structure can be readily seen (FIG. 12A). However, in a two-immiscible-oil mixed emulsion, if O1 has a mass density $\rho_{O1}$ that is greater than $\rho_c$, and O2 has a mass density $\rho_{O2}$ that is less than $\rho_c$, then the axis of a Janus droplet, formed as a result of fusion, can lie perpendicular to the plane of observation in the microscope images (FIG. 12B). This buoyancy effect makes a linear Janus structure (O1-O2)/W more difficult to detect, and it could even lead to misinterpretation of one droplet being engulfed inside the other (e.g. (O1/O2)/W). To rule out the possibility of an engulfed droplet structure, we have used laser tweezers to re-orient the fused droplet structure and unambiguously identify that it is a linear Janus droplet.

FIGS. 12A-12C show optical micrographs of Janus droplet structures after inducing fusion. Conditions: $C_{SDS}$=5 mM, $\phi_T$=0.02, $C_{CTAB}$=5 mM, and $\chi_{SDS}$=0.7. FIG. 12 a shows a PFPMS droplet fused with a PPPMS droplet. FIG. 12B shows a PFPMS droplet fused with a squalene droplet in a linear Janus structure. Because PFPMS has a mass density greater than water and squalene has a mass density less than water, the axis of the linear Janus droplet preferentially orients perpendicular to the focal plane (i.e. out of the page). Laser tweezers are used to re-orient the Janus droplet and show that the structure is not engulfed. FIG. 12C shows a PDMS droplet (left) fused with solid ghee (right). Scale bars are 10 µm.

Figures 13A, 13B, 13C:
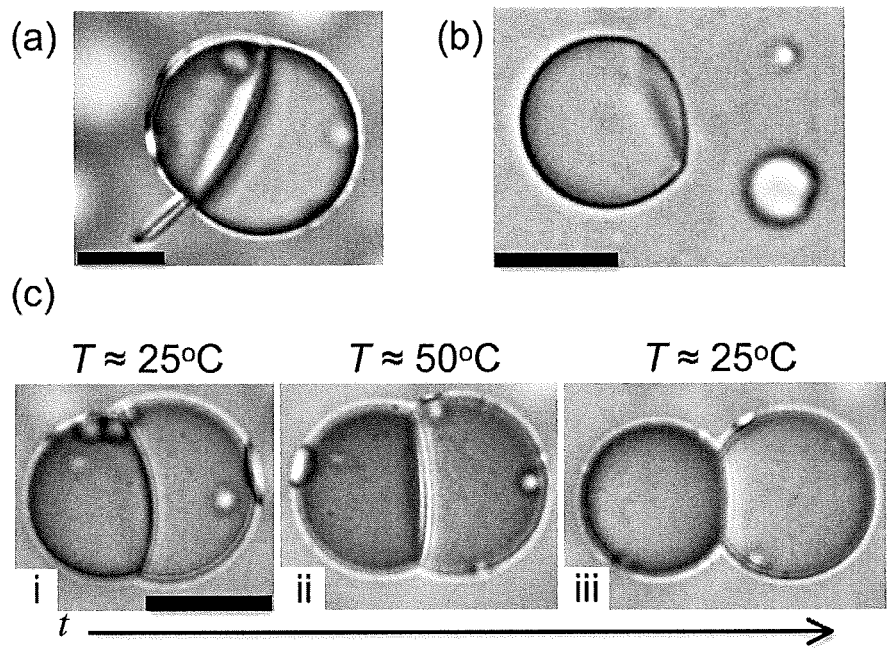
FIGS. 13A-13C show that solid anionic-cationic surfactant complexes create complicated time-dependent and temperature-dependent structures in mixed emulsion and mixed surfactant systems.

Over time, droplets in fused mixed surfactant systems can exhibit evidence of a solid surfactant-complexed crystal film that can exist between O1-O2 interfaces and at O/W interfaces. For example, Janus droplets occasionally develop a crystal protruding from their O1-O2 interfaces (FIG. 13A). Isolated single droplets can also develop flat facets (FIG. 13B) suggesting crystal growth can occur on their O/W interfaces and affect droplet morphology as well. Additional evidence of crystal film formation at the O1-O2 interface of Janus droplets is provided by temperature cycling (see Methods). A soybean oil, PDMS Janus droplet is shown at T≈25° C. before heating (FIG. 13C—panel i), at T≈50° C. (FIG. 13C—panel ii), and T≈25° C. after cooling (FIG. 13C—panel iii). The contact angle changes dramatically before and after heating. These pieces of evidence related to surfactant crystal formation suggest that a solid interfacial film of crystallized surfactant can exist at or between the O1-O2 interface, leading to rigidity of the fused droplet structures.

FIGS. 13A-13C show that solid anionic-cationic surfactant complexes create complicated time-dependent and temperature-dependent structures in mixed emulsion and mixed surfactant systems. FIG. 13A shows observed protrusion of a large surfactant crystal from an oil-oil interface of a soybean oil/PDMS Janus droplet 5 days after fusion. FIG. 13B shows flat facets observed on single droplets 12 days after soybean oil/PDMS fusion. FIG. 13C shows temperature history affects the oil-oil interfacial structures of a fused Janus droplet: $C_{SDS}$=5 mM, $\phi$=0.02 soybean oil emulsion and PDMS emulsion using $C_{CTAB}$=5 mM at $\chi_{SDS}$=0.7. Janus droplet is shown initially at T≈25° C. (left), at 50° C. (middle), and back at 25° C. (right) after temperature cycling. The temperature is held fixed at least 20 minutes before micrographs are taken. Micrograph scale bars are 10 µm.

Figure 14:
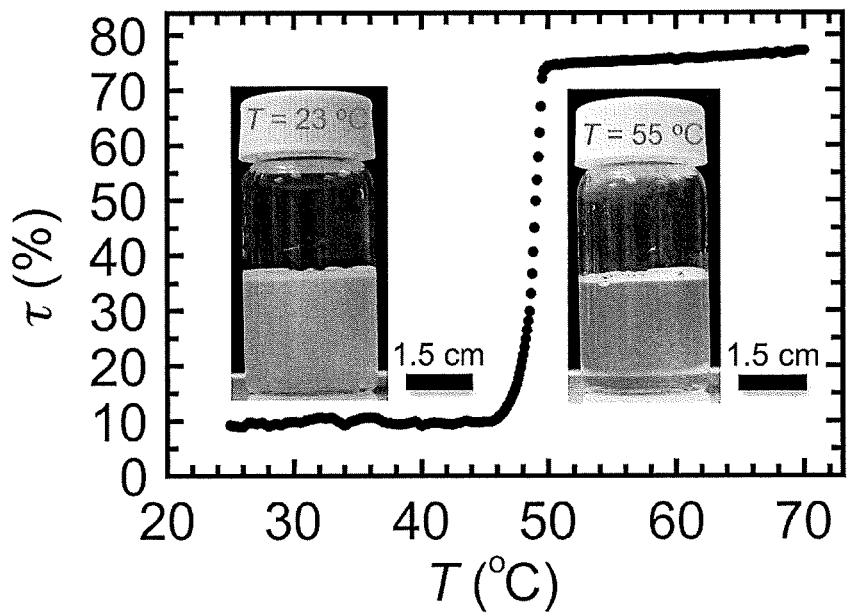
FIG. 14 shows a graph of transmission, $\tau$, as a function of temperature, T, for a surfactant mixture of 5 mM SDS and 5 mM CTAB ($\phi$=0) at $\chi_{SDS}$=0.7 at a light wavelength $\lambda$=600 nm.

The surfactant crystals can dissolve when heated, so we measure the transmission, τ, as a function of T for a solution of SDS-CTAB mixed surfactants (i.e. $\phi$=0) at $\chi_{SDS}$=0.7 (FIG. 14). At room temperature, the initial solution appears cloudy (FIG. 14—left inset), whereas the heated solution appears translucent (FIG. 14—right inset). The crystals dissolve at $T_d$≈50° C. Therefore, when a Janus droplet, as shown in FIG. 13C (left), is heated beyond $T_d$, the contact angle changes significantly, as shown in FIG. 13C (middle); it is possible that a rigid interfacial crystal film, which is difficult to identify using optical microscopy, between the two immiscible oils dissolved. Upon cooling back to room temperature, the two halves of the Janus droplet remain together, but the contact angle is very different, so there is temperature hysteresis in the contact angle (FIG. 13C—right).

FIG. 14 shows a graph of transmission, τ, as a function of temperature, T, for a surfactant mixture of 5 mM SDS and 5 mM CTAB ($\phi$=0) at $\chi_{SDS}$=0.7 at a light wavelength λ=600 nm. We identify an effective dissolution temperature $T_d$≈50° C. of crystalline surfactant complexes that scatter visible light. Insets show photographs of the mixtures at T≈23° C. (left) and ≈55° C. (right).

Since the phase behavior of the surfactant mixtures, which is a function of temperature, could play a role in the droplet fusion process, we have attempted to create droplet fusion in a mixed emulsion system of soybean oil and PDMS at T≈60° C., above the effective dissolution transition point $T_d$≈50° C. of the cationic-anionic surfactant complexes that scatter visible light, as shown in FIG. 14. Optical microscopy observations indicate that there is very little to no observable droplet fusion for $\chi_{SDS}$=0.7 for both $\phi$=0.02 and $\phi$=0.2 at this elevated temperature above $T_d$. Thus, we link the existence and rate of self-limiting droplet fusion reactions in emulsions to the temperature-dependent behavior of the surfactant mixtures in forming supramolecular cationic-anionic complexes, such as those that can scatter visible light significantly. Moreover, at temperatures T<$T_d$, it is possible for solid complexed SDS-CTAB crystals to nucleate and grow on droplet interfaces, and these solid films could play a role in the resulting stability and morphology of fused droplets. The formation of such solid surfactant films on droplet interfaces could be an important mechanism that can be used to re-stabilize droplets having the same oil type against further coalescence in a self-limiting fusion reaction.

Figures 15A, 15B, 15C:
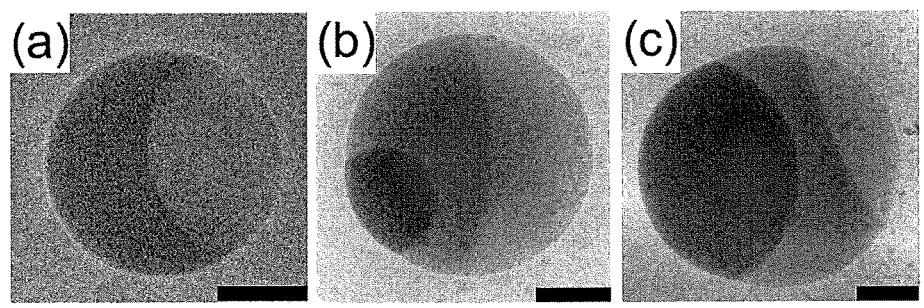
FIGS. 15A-15C show cryo-transmission electron micrographs of Janus and Cerberus nanodroplets created by surfactant-induced droplet fusion.

We have also formed compound droplet structures in mixed nanoemulsion systems having two or three immiscible oils. In FIG. 15A, we show a cryo-TEM micrograph of a Janus nanodroplet composed of soybean oil and PDMS. Because PDMS, which contains silicon as part of its backbone, has a higher average atomic number density than soybean oil, a hydrocarbon, then PDMS appears darker than soybean oil in cryo-TEM images. Thus, the left part of the Janus droplet is PDMS and the right part is soybean oil. Because the Janus droplet is nearly spherical, the external interfacial tensions of soybean oil-water and PDMS-water are much larger than the internal interfacial tension associated with the curved soybean oil-PDMS interface. In FIGS. 15B and 15C, we show cryo-TEM images of Cerberus droplets created using three immiscible oils: PFPMS, POMS, and PPPMS. Based on the atomic number density of the oils, we deduce that the light gray region of the droplet is POMS, the medium gray region is PPPMS, and the darkest region is fluorinated PFPMS. In FIG. 15B, the POMS/PPPMS interface is convex with respect to the PPPMS, whereas the same interface is concave in FIG. 15C. Also, there is a noticeable discontinuity in the outline of the compound droplet at the contact line where the PPPMS, PFPMS, and water meet; this discontinuity is most apparent in FIG. 15C, as the PFPMS seems to protrude from the core. The non-spherical shape of the Cerberus droplet and the discontinuity in its outline in FIG. 15C indicates that the internal interfacial tension of the PFPMS and PPPMS is not much smaller than that of the oil-water interfacial tensions. Thus, internal oil-oil interfacial tensions as well as line tensions must be properly included in any energy minimization theory that would attempt to predict the interfacial shapes and areas of Cerberus nanodroplets.

FIGS. 15A-15C show cryo-transmission electron micrographs of Janus and Cerberus nanodroplets created by surfactant-induced droplet fusion. FIG. 15A shows a Janus droplet of PDMS (darker convex-concave lens)-soybean oil (lighter biconvex lens) at $\chi_{SDS}$=0.7. Scale bar: 100 nm. FIG. 15B shows a Cerberus droplet composed of PFPMS (darkest lens region), PPPMS (middle lens region), POMS (lightest lens region). Scale bar: 200 nm. FIG. 15C shows a Cerberus droplet composed of PFPMS, PPPMS, and POMS (from left to right). Curvatures of the PPPMS and POMS lens regions differ significantly from those in part 15B and the droplet appears to be asymmetric and elongated. Scale bar: 200 nm.

By contrast to the optical microscopy experiments involving microscale emulsions, in the CTEM micrographs of fused nanoscale droplets, we do not see direct evidence for complexed surfactant crystals at internal O/O interfaces of Janus or Cerberus droplets, or on external droplet O/W interfaces, at least for droplets examined by cryo-TEM at similar magnification one day after the fusion. For the same fixed SDS concentration, because the nanoscale droplets have a much larger total interfacial area than their microscale counterparts, more SDS resides on nanodroplet interfaces through adsorption rather than remaining in the bulk continuous phase prior to adding the CTAB. Also, the higher curvature of the oil interfaces on the nanoscale droplets might inhibit growth of noticeable crystals, especially if the crystals prefer to form in rigid planar structures that have little curvature. In addition, the nanoscale interfacial area between nanoscale oil droplets is very small, so the fusion of the oils may happen rapidly, precluding surface crystallization between the different oil types. Overall, the external oil-water interfaces of the multi-component nanoemulsion droplets are much closer to spherical in shape, as compared to the external interfaces of microscale droplets.

Similar immiscible-oil systems may have different morphologies depending on the specific non-equilibrium pathway in which droplets are fused. For example, the Cerberus droplets that we have produced have a linear singlet POMS-PPPMS-PFPMS morphology. However, Cerberus droplets produced using the same set of immiscible oils by flow-induced fusion, instead form a dominantly engulfed-linear (PFPMS/PPPMS)-POMS Cerberus morphology. Based on previous interfacial tension measurements[21] using only 5 mM SDS (i.e. not a mixed surfactant system that also contains CTAB), neglecting line energies, which have not been measured, it would be energetically favorable for the PFPMS to maintain more interfacial area in contact with water than with PPPMS. The strong flows used in flow-induced fusion permit access to such engulfed states. However, here, in the case of surfactant-induced droplet fusion, where flows are much weaker, our observations show that the PFPMS can become a part of a linear PFPMS-PPPMS-POMS Cerberus droplet structure, rather than being engulfed. We speculate that the extreme flow required for flow-induced fusion may overcome this high energy cost of surfactant desorption, leading to a preference of engulfed droplet structures, whereas the surfactant-induced fusion method tends to provide a pathway for selecting non-engulfed droplet morphologies. In principle, for mixed emulsions containing two or more immiscible oils, flow-induced fusion could produce non-engulfed multi-component droplet structures and surfactant-induced fusion could produce engulfed multi-component droplet structures, depending on interfacial, line, and desorption energies and the method and history of interfacial destabilization leading to fusion.

Conclusion

Self-limiting droplet fusion of ionic emulsions provides a convenient and flexible means of causing and controlling massively parallel coalescence and fusion of droplets. By tuning $\chi$ and $\phi$, it is possible to achieve reaction conditions ranging from very little droplet fusion to nearly complete macroscopic oil breakout. Moreover, the self-limiting droplet reactions can be readily scaled up to large volumes of emulsions. These reactions can be produced in a variety of means, such as adding a solution of oppositely charged surfactant to an ionic emulsion, as we have focused on here, or by adding a cationically stabilized emulsion to an anionically stabilized emulsion, yet preserving an adequate excess of at least one surfactant type so that near-neutralization is avoided and the resulting droplet structures can re-stabilize through residual charge repulsion provided by the surfactant excess. In the simplest case of a single emulsion, self-limiting coalescence of monodisperse droplets can be used to create a distribution of droplet sizes that has discrete peaks corresponding to the fusion of integral numbers of droplets.

For microscale droplets, the formation of at least partially neutralized surfactant complexes, containing both anionic and cationic surfactant molecules, especially at droplet interfaces, can be an important factor in determining the morphology of resulting droplets. Under certain conditions, such complexes appear to impart an elastic rigidity to the outer oil-water and inner oil-oil interfaces of droplets. Thus, we infer that a solid layer of complexed surfactant can be found either at oil-water interfaces or, if fully neutralized, at oil-oil interfaces. In addition, microscopic observations made while cycling the temperature cycling reveal that the oil-oil interfaces between Janus droplets containing immiscible oils can be strongly history dependent. Moreover, we have characterized the microsecond time scale associated with the merger of immiscible microscale droplets using high-speed optical microscopy.

For nanoscale droplets, self-limiting reactions of ionic emulsions presents an alternative route to forming Janus, Cerberus, and more complex droplet structures than flow-induced droplet fusion. Using oppositely charged surfactant to cause fusion of an ionically stabilized nanoemulsion yields distinctly different morphologies (i.e. O1-O2-O3) than flow-induced fusion (i.e. (O3/O1)-O2). Thus, for ionic multi-oil nanoemulsions, the history of flow and the history of exposure to surfactants having opposite charge are different out-of-equilibrium pathways that can produce complex multi-compartment nanodroplets of immiscible oils. It is possible that a combination of the two transient destabilization approaches can yield access to and control over hypothesized out-of-equilibrium nanodroplet structures that have not yet been observed.

Based on our experiments involving droplets of two or more immiscible oils, we anticipate that self-limiting droplet fusion of ionic emulsions can be used to create large numbers of compound droplets that have highly complex structures and extended interfacial connectivity, including percolating network structures. Moreover, we have shown that self-limiting reactions can be created between charge-stabilized liquid droplets of immiscible oils as well as between liquid droplets and solid colloidal objects, such as solidified ghee. Thus, we anticipate that the approach of creating self-limiting fusion reactions in a wide range of colloidal dispersions of objects stabilized by either anionic or cationic groups, which can be either chemically bound (i.e. covalently) to particle surfaces or physically bound (i.e. adsorbed as surfactants), using an oppositely charged surfactant solution is quite general and will find other applications.

Further experimental studies are needed to characterize the distribution of surfactants in the bulk and on the various interfaces of droplets as the transient droplet destabilization, which results from at least partial surface-charge neutralization, occurs. For instance, performing time-resolved x-ray crystallography on mixtures of anionic and cationic surfactant solutions immediately after mixing, as well as on ionic emulsions that are combined with oppositely charged surfactant solutions, could reveal the kinetics of formation of surfactant complexes, including rigid crystals. Moreover, additional experimental microscopy studies of droplet fusion reactions as a function of $\phi$ of different droplet types, $\chi$ for different cationic-anionic surfactant pairs, T, and mixing conditions could provide additional data that would be useful for comparison with any multi-scale theories that may be developed to describe this effect.

Furthermore, in some embodiments, the resulting droplets can be compartmentalized, rather than segmented. For instance, although we show examples of segmented droplets, it is possible to also obtain engulfed droplets. The compartmentalized droplets have distinguishable internal interfaces between at least a first droplet liquid and a second droplet liquid within a given compartmentalized droplet. Examples of compartmentalized droplets are engulfed droplets, segmented droplets, and/or segmented plus engulfed droplets (when there are 3 or more droplet liquids).

Also, prior art has shown coalescence of emulsion droplets induced using ionic agents such as NaCl, but we specifically are using ionic amphiphilic molecules, such as surfactants that have head groups that have the opposite sign of charge compared to the amphiphilic molecules used to stabilize the droplets prior to fusion. The tails of these amphiphilic molecules attract each other through hydrophobic interactions, so it is even more likely that neutralization of surface charge on the droplets will occur compared to a simple ionic agent such as NaCl.

Example 3: Additional Embodiments

In an embodiment of the current invention, at least one of sub-microscale and nanoscale oil-in-water emulsions having multi-component internally compartmentalized oil droplets are made by a multi-step process involving at least coalescence of two or more droplets of immiscible oils, wherein said coalescence is caused by an energetic excitation stronger than a thermal excitation, wherein said energetic excitation overcomes a stabilizing repulsion between droplets.

We provide a first oil (O1), a second oil (O2), and a third oil (O3), each oil being mutually immiscible with the other oils. The first oil, the second oil, and the third oil are also all immiscible with an aqueous stabilizing solution of a stabilizer (e.g. a surfactant, a lipid, an amphiphilic diblock copolymer). Into the first oil, we dissolve molecules of a first oil-soluble drug that is soluble in the first oil but not in at least one of the second oil and the third oil. Into the second oil, we dissolve molecules of a second oil-soluble drug that is soluble in the second oil but not in at least one of the first oil and the third oil. Into the third oil, we dissolve molecules of a third oil-soluble drug that is soluble in the third oil but not in at least one of the first oil and the second oil. We call the first oil into which molecules of the first oil-soluble drug have been dissolved the first drug-loaded oil. Likewise, we call the second oil into which molecules of the second oil-soluble drug have been dissolved the second drug-loaded oil. Likewise, we call the third oil into which molecules of the third oil-soluble drug have been dissolved the third drug-loaded oil.

We provide stabilizing molecules of at least one type of stabilizer, such as amphiphilic small molecules, surfactants, lipids, amphiphilic polymers, and amphiphilic block co-polymers, that are soluble or at least partially soluble in at least one of water, said first oil, said second oil, and said third oil. When the aqueous stabilizing solution is placed in contact with at least one of said first oil, said second oil, and said third oil, to form an oil-water interface, then at least some of said stabilizing molecules preferentially adsorb onto said oil-water interface. Such adsorbed stabilizing molecules provide a stabilizing repulsive interaction (i.e. repulsion) between a first oil-water interface with adsorbed stabilizing molecules and a second oil-water interface with adsorbed stabilizing molecules, inhibiting coalescence of the first and second oil-water interfaces in the presence of thermal fluctuations, irrespective of a curvature of said first and second oil-water interfaces. At least one of a type of a stabilizing molecule and a concentration of a stabilizing molecule in said stabilizing solution is adjusted such that said first and second oil-water interfaces also remain stable and do not coalesce in the presence of a first applied flow stress that is less than a stabilizing repulsive stress between said first and second oil-water interfaces.

In an embodiment of the current invention, said stabilizing solution is an aqueous stabilizing solution, in which at least one type of said stabilizing molecules have been placed in contact with water and at least a portion of said stabilizing molecules have been solubilized by water.

Using said aqueous stabilizing solution as a continuous aqueous phase and said first drug-loaded oil as a first dispersed oil phase, we form a first oil-in-water premix emulsion of said first drug-loaded oil at a first oil volume fraction by causing a first droplet rupturing of said first dispersed oil phase into said continuous aqueous phase using a first emulsification device. Likewise, using said aqueous stabilizing solution as a continuous aqueous phase and said second drug-loaded oil as a second dispersed oil phase, we form a second oil-in-water premix emulsion of said second drug-loaded oil at a second oil volume fraction by causing a first droplet rupturing of said second dispersed oil phase into said continuous aqueous phase using said first emulsification device. Likewise, using said aqueous stabilizing solution as a continuous aqueous phase and said third drug-loaded oil as a third dispersed oil phase, we form a third oil-in-water premix emulsion of said third drug-loaded oil at a third oil volume fraction by causing a first droplet rupturing of said third dispersed oil phase into said continuous aqueous phase using said first emulsification device.

In an embodiment of the current invention, said first emulsification device is at least one of a membrane emulsification device, a microfluidic device, a homogenizer, an ultrasonic device, a spray device, an atomizer, an electrospray device, a stirring device, a milling device, an injection couette device, and a mixing device.

In an embodiment of the current invention, consequent to said first droplet rupturing, said first emulsification device has caused the formation of said first, second, and third oil-in-water premix emulsions, wherein droplets in each of said premix emulsions have an average droplet radius that is larger than about one micron.

We combine a first volume $V_1$ of said first oil-in-water premix emulsion of said first drug-loaded oil, a second volume $V_2$ of said second oil-in-water premix emulsion of said second drug-loaded oil, and a third volume $V_3$ of said third oil-in-water premix emulsion of said third drug-loaded oil to form a composite premix emulsion having a total composite premix volume of $V_{tot}=V_1+V_2+V_3$ which has a total oil volume fraction $\phi_{tot}=(V_1\phi_1+V_2\phi_2+V_3\phi_3)/V_{tot}$ in said aqueous continuous phase.

In an embodiment of the current invention, the first, second, and third oil-in-water premix emulsions are put into contact in a beaker and subjected to mild stirring to ensure that the droplets of each drug-loaded oil are evenly distributed in the common aqueous continuous phase of the composite premix emulsion. Said mild stirring serves only to evenly distribute droplets of each of the drug-loaded oils; said mild stirring does not overcome the interfacial repulsion between droplets to cause droplet coalescence in said composite premix emulsion. Likewise, said mild stirring does not create flow stresses that are high enough to overcome the Laplace pressure of the droplets and cause droplets in said composite premix emulsion to rupture.

In an embodiment of the current invention, the purpose of making said composite premix emulsion is to provide a uniform liquid emulsion input into an emulsification device, such as a high-pressure microfluidic homogenizer, that has a length-scale associated with a microfluidic geometry that is larger than an average droplet diameter of said composite premix emulsion.

Said composite premix emulsion is inputted fluidically to a second emulsification device, such as a homogenizer, a microfluidic homogenizer, a high-pressure homogenizer, an ultrasonic homogenizer, a high-speed colloid mill, a nanofluidic device. Said second emulsification device is typically capable of rupturing larger microscale droplets into at least one of sub-micron and nanoscale droplets. On said second emulsification device, controls and geometries are adjusted such that the conditions created in said second emulsification device causes at least coalescence of a first oil-water interface with adsorbed stabilizing molecules of a first oil droplet with a second oil-water interface with adsorbed stabilizing molecules of a second oil droplet. For example, when using a high-pressure microfluidic homogenizer, a liquid pressure is typically adjusted to be above about 5,000 psi and a microfluidic channel dimension of a Y-type interaction chamber is chosen to be less than about 100 microns.

In an embodiment of the current invention, said controls and geometries of said second emulsification device are adjusted to cause a high degree of droplet coalescence, so that a droplet of said first drug-loaded oil coalesces with (i.e. combines with) a droplet of said second drug-loaded oil to form a double drug-loaded oil droplet of said first and second drug-loaded oils. In addition, said second emulsification device causes said double drug-loaded oil droplet to coalesce with a droplet of a third drug-loaded oil to form a triple drug-loaded oil droplet.

In an embodiment of the current invention, said second emulsification device causes sufficient droplet coalescence to cause the formation of predominantly triple drug-loaded oil droplets.

In an embodiment of the current invention, said second emulsification device is a high-pressure microfluidic homogenizer that creates extreme flow stresses (e.g. shear and/or extensional stresses) that overcome interfacial repulsions between droplet interfaces populated with adsorbed stabilizer molecules, yielding substantial droplet coalescence, irrespective of the type of oil or oils inside the droplets.

In an embodiment of the current invention, the type of interfacial structure within said triple drug-loaded oil droplet containing said first, second, and third drug-loaded oils, resulting from at least a first and a second droplet coalescence event, is at least one of a type of interfacial structure described in FIGS. 5A-5G.

In an embodiment of the current invention, beyond causing at least some droplet coalescence, said second emulsification device also causes droplet rupturing of at least one of said first droplet of said first drug-loaded oil, said second droplet of said second drug-loaded oil, said third droplet of said third drug-loaded oil, said double drug-loaded droplet, and said triple drug-loaded droplet. For example, if said second emulsification device is a high-pressure microfluidic homogenizer, then said high-pressure microfluidic homogenizer produces high enough flow stresses to cause bigger droplets, including combined double- and triple-droplets resulting from coalescence, to rupture into smaller droplets via a capillary instability. Because continuing droplet coalescence events in said second emulsification device necessary cause the resulting combined droplets to increase in size by volume conservation, then such larger droplets may be more easily ruptured by said second emulsification device (e.g. as rupturing driven via a flow-induced capillary instability that overcomes a droplet Laplace pressure, such as has been described by G. I. Taylor and others), thereby preventing coarsening of the emulsion and growth in the average droplet radius.

In an embodiment of the current invention, the type of interfacial structure within said triple drug-loaded oil droplet containing said first, second, and third drug-loaded oils is at least one of a type of interfacial structure described in FIGS. 5A-5G.

In an embodiment of the current invention, said triple-drug-loaded oil droplet is a Cerberus droplet having an engulfed-linear interfacial structure that has a sub-micron maximum dimension in a cryo-TEM image similar to that shown in FIG. 1.

In an embodiment of the current invention, the type of interfacial structure within said triple drug-loaded oil droplet containing said first, second, and third drug-loaded oils, as depicted in FIGS. 5A-5G, is selected by at choosing oil 1, oil 2, oil 3, and an aqueous continuous phase which may contain stabilizing molecules, wherein at least one of a O1-O2 interfacial tension, a O1-O3 interfacial tension, a O2-O3 interfacial tension, a O1-continuous phase interfacial tension, a O2-continuous phase interfacial tension, a O3-continuous phase interfacial tension, a O1-O2-continuous phase line tension, a O1-O3-continuous phase line tension, a O2-O3-continuous phase line tension, and a O1-O2-O3 line tension causes a selection of a preferred interfacial structure of said triple drug-loaded oil droplet.

In an embodiment of the current invention, subsequent to said coalescence of said drug-loaded droplets induced by said second emulsification device, the resulting said triple drug-loaded oil droplets remain stable against coalescence when subjected to quiescent thermal excitations.

In an embodiment of the current invention, the temperature of said second emulsification device is controlled to prevent heating of said composite premix emulsion being processed into said triple drug-loaded oil droplets beyond a desired temperature in order to preserve the efficacy of at least one of said drug molecules in at least one of said drug-loaded oils.

In an embodiment of the current invention, subsequent to at least said droplet coalescence induced by said second emulsification device, an average maximum droplet dimension of said triple drug-loaded droplets is less than one micron, yielding a submicron triple drug-loaded emulsion.

In an embodiment of the current invention, subsequent to at least said droplet coalescence induced by said second emulsification device, an average maximum droplet dimension of said triple drug-loaded droplets is less than two hundred nanometers, yielding a nanoscale triple drug-loaded emulsion.

In an embodiment of the current invention, at least one of said first, second, and third oils is at least one of a hydrocarbon oil, an aliphatic oil, a partially aliphatic oil, an aromatic oil, a partially aromatic oil, a silicone oil, a siloxane oil, a partially siloxane oil, a poly-siloxane oil, a halogenated oil, a partially halogenated oil, a fluorinated oil, a fluorinated silicone oil, a fluorinated hydrocarbon oil, a chlorinated oil, a brominated oil, an iodized oil, a plant oil, an animal oil, a fungus oil, a fish oil, a nut oil, a seed oil, a copolymer oil, a branched polymer oil, a branched copolymer oil, a distilled oil, a purified oil, a sterilized oil, a blended oil, a derivatized oil, an anisotropic oil, a lyotropic liquid crystal, a thermotropic liquid crystal, a ferrofluid oil, a nanoparticle-dispersed oil, a non-polar oil, and a polar oil. Specific examples of such oils are listed in product catalogs of companies such as Sigma-Aldrich, Gelest, Cambridge Isotopes, Merck, DuPont, and Cargill.

In an embodiment of the current invention, at least one of said first, second, and third oils is selected to confer a property of at least partial solubility to at least high solubility of at least one of a first, second, and third drug molecules in at least one of said first, second, and third oils at standard temperature and pressure.

In an embodiment of the current invention, at least one of said stabilizing molecules is at least one of an amphiphilic molecule, a surfactant molecule, a halogenated surfactant molecule, an ionic surfactant molecule, a non-ionic surfactant molecule, a zwitterionic surfactant molecule, a polymeric surfactant molecule, a di-block copolymer molecule, a tri-block copolymer molecule, a pluronic molecule, a poly-ethyleneglycol (PEG) containing molecule, a fluorinated surfactant molecule, an amphiphilic cluster, an amphiphilic siloxane molecule, a protein molecule, a membrane protein molecule, a viral coat protein molecule, a cell-targeting protein molecule, an antibody molecule, an antigen molecule, and a lipid molecule.

In an embodiment of the current invention, a rate of droplet coalescence (i.e. fusion) in said second emulsification device is controlled through at least one of a type of stabilizer molecules, a concentration of stabilizer molecules, a temperature, a microfluidic geometry, a microfluidic channel dimension, a total droplet volume fraction, an average droplet dimension, an applied pressure, an applied flow stress, and an applied flow rate.

In an embodiment of the current invention, a rate of droplet rupturing (i.e. fission) in said second emulsification device is controlled through at least one of a type of stabilizer molecules, a concentration of stabilizer molecules, a temperature, a microfluidic geometry, a microfluidic channel dimension, a total droplet volume fraction, an average droplet dimension, an applied pressure, an applied flow stress, and an applied flow rate.

In an embodiment of the current invention, an aqueous dispersion of triple drug-loaded oil droplets is a nanoscale triple drug-loaded emulsion, wherein each droplet has the capacity to co-locally deliver said first, second, and third drug molecules to at least one of a virus, a sub-cellular biological structure, a nucleus of a biological cell, a cytoplasm of a biological cell, a biological membrane, a biological tissue, a biological organ, a biological organism, and a biological colony.

In an embodiment of the current invention, at least one of said first, second, and third oils is loaded with at least one of an imaging contrast enhancement agent, an isotopic molecule, a radioisotopic molecule, an acidic molecule, a basic molecule, at bio-regulating molecule, a molecular complex, a fluorescent molecule, a vitamin molecule, a nutrient molecule, a endocytosis-inducing agent, an apoptosis-inducing agent, a hydrophobic peptide, a hydrophobic polypeptide, a block co-polypeptide that has at least a hydrophobic block, and a hydrophobic protein.

In an embodiment of the current invention said imaging contrast enhancement agent is suitable for detection by at least one of nuclear magnetic resonance, positron emission tomography, x-ray imaging, ultrasonic imaging, electromagnetic imaging, optical fluorescence imaging, and optical scattering.

In an embodiment of the current invention, a first drug-loaded oil is at least a partially fluorinated oil that is loaded with at least a fluorinated drug molecule.

In an embodiment of the current invention, a first drug-loaded oil is an iso-alkane that is loaded with at least an aliphatic drug molecule.

In an embodiment of the current invention, a first drug molecule is at least one of an anti-inflammatory drug molecule, a bio-regulating drug molecule, an anti-microbial drug molecule, an anti-cancer drug molecule, an anti-cholesterol drug molecule, an anti-septic drug molecule, an anti-metabolite molecule, a nutrient molecule, an inhibitor molecule, a promoter molecule, a hydrophobic protein molecule, a hydrophobic amino acid molecule, a hydrophobic poly-amino acid molecule, and a steroid molecule.

In an embodiment of the current invention, a first drug molecule is a steroid molecule. Examples of steroid molecules include but are not limited to the following: a sterol molecule, a steroid hormone molecule, a corticosteroid molecule, an anabolic steroid molecule, a glucocorticoid molecule, a mineralocorticoid molecule, a testosterone molecule, an androgen molecule, an estrogen molecule, a progestogen molecule, an ectdysteroid molecule, a phytosterol molecule, a brassinosteroid molecule, a steroidal alkyloid molecule, and a ergosterol molecule.

In an embodiment of the current invention, a second drug molecule is an anti-microbial drug molecule. Examples of anti-microbial drug molecules include but are not limited to: an anti-biotic molecule, an anti-fungal molecule, an anti-viral molecule, an anti-septic molecule, an anti-microbial peptide, an anti-microbial polypeptide, and an anti-bacterial molecule.

In an embodiment of the current invention, a third drug molecule is an anti-cancer drug molecule that is at least partially hydrophobic. Examples of anti-cancer drug molecules are listed at the National Institute of Health's website: http://www.cancer.gov/cancertopics/druginfo/alphalist. Such anti-cancer drug molecules include but are not limited to: a paclitaxel, a 5-fluorouracil, a hydroxycamptothecin, a doxorubicin, a cisplatin, a daunorubicin, an etopopside, a vinblastine, a vincristine, a mercaptopurine, and a methotrexate.

Alternative Embodiment of the Current Invention

In an alternative embodiment of the current invention, we provide a first oil (O1) and a second oil (O2), each oil being mutually immiscible with the other oil. The first oil and the second oil are also all immiscible with an aqueous stabilizing solution of stabilizer molecules (e.g. a surfactant, a lipid, an amphiphilic diblock copolymer). Into the first oil, we dissolve molecules of a first oil-soluble drug that is soluble in said first oil but not substantially soluble in said second oil. Into said second oil, we dissolve molecules of a second oil-soluble drug that is soluble in said second oil but not in said first oil. We call the first oil into which molecules of the first oil-soluble drug have been dissolved the first drug-loaded oil. Likewise, we call the second oil into which molecules of the second oil-soluble drug have been dissolved the second drug-loaded oil.

We provide stabilizing molecules of at least one type of stabilizer, such as amphiphilic small molecules, surfactants, lipids, amphiphilic polymers, and amphiphilic block co-polymers, that are soluble or at least partially soluble in at least one of water, said first oil, and said second oil to form a stabilizing solution.

When said stabilizing solution is placed in contact with at least one of said first oil and said second oil to form an oil-water interface, then at least some of said stabilizing molecules preferentially adsorb onto said oil-water interface. Such adsorbed stabilizing molecules provide a stabilizing repulsive interaction (i.e. repulsion) between a first oil-water interface with adsorbed stabilizing molecules and a second oil-water interface with adsorbed stabilizing molecules, inhibiting coalescence of said first and second oil-water interfaces in the presence of thermal fluctuations, irrespective of a curvature of said first and second oil-water interfaces.

In an embodiment of the current invention, said stabilizing molecules dissolve substantially in said water, but not in said first oil and said second oil, to form an aqueous stabilizing solution.

In an embodiment of the current invention, said stabilizing solution is an aqueous stabilizing solution, in which at least one type of said stabilizing molecules have been placed in contact with water and at least a portion of said stabilizing molecules have been solubilized by water.

In an embodiment of the current invention, at least a portion of said stabilizing molecules is hydrophilic.

In an embodiment of the current invention, at least one of a type of a stabilizing molecule and a concentration of a stabilizing molecule in said stabilizing solution is adjusted such that said first and second oil-water interfaces also remain stable and do not coalesce in the presence of a first applied flow stress that is less than a stabilizing repulsive stress between said first and second oil-water interfaces.

Using said aqueous stabilizing solution as a continuous aqueous phase and said first drug-loaded oil as a first dispersed oil phase, we form a first oil-in-water premix emulsion of said first drug-loaded oil at a first oil volume fraction by causing a first droplet rupturing of said first dispersed oil phase into said continuous aqueous phase using a first emulsification device. Likewise, using said aqueous stabilizing solution as a continuous aqueous phase and said second drug-loaded oil as a second dispersed oil phase, we form a second oil-in-water premix emulsion of said second drug-loaded oil at a second oil volume fraction by causing a first droplet rupturing of said second dispersed oil phase into said continuous aqueous phase using said first emulsification device.

In an embodiment of the current invention, said first emulsification device is at least one of a membrane emulsification device, a microfluidic device, a homogenizer, an ultrasonic device, a spray device, an atomizer, an electrospray device, a stirring device, a milling device, an injection couette device, and a mixing device.

In an embodiment of the current invention, consequent to said first droplet rupturing, said first emulsification device has caused the formation of said first and second oil-in-water premix emulsions, wherein droplets in each of said premix emulsions have an average droplet radius that is larger than about one micron.

We combine a first volume $V_1$ of said first oil-in-water premix emulsion of said first drug-loaded oil and a second volume $V_2$ of said second oil-in-water premix emulsion of said second drug-loaded oil to form a composite premix emulsion having a total composite premix volume of $V_{tot}=V_1+V_2$ which has a total oil volume fraction $\phi_{tot}=(V_1\phi_1+V_2\phi_2)/V_{tot}$ in said aqueous continuous phase.

In an embodiment of the current invention, said first and second oil-in-water premix emulsions are put into contact in a beaker and subjected to mild stirring to ensure that the droplets of each drug-loaded oil are evenly distributed in the common aqueous continuous phase of the composite premix emulsion. Said mild stirring serves only to evenly distribute droplets of each of the drug-loaded oils; said mild stirring does not overcome the interfacial repulsion between droplets to cause droplet coalescence in said composite premix emulsion. Likewise, said mild stirring does not create flow stresses that are high enough to overcome the Laplace pressure of the droplets and cause droplets in said composite premix emulsion to rupture.

In an embodiment of the current invention, the purpose of making said composite premix emulsion is to provide a uniform liquid emulsion input into an emulsification device, such as a high-pressure microfluidic homogenizer, that has a length-scale associated with a microfluidic geometry that is larger than an average droplet diameter of said composite premix emulsion.

Said composite premix emulsion is inputted fluidically to a second emulsification device, such as a homogenizer, a microfluidic homogenizer, a high-pressure homogenizer, an ultrasonic homogenizer, a high-speed colloid mill, a nanofluidic device. Said second emulsification device is typically capable of rupturing larger microscale droplets into at least one of sub-micron droplets and nanoscale droplets. On said second emulsification device, controls and geometries are adjusted such that the conditions created in said second emulsification device causes at least coalescence of a first oil-water interface with adsorbed stabilizing molecules of a first oil droplet with a second oil-water interface with adsorbed stabilizing molecules of a second oil droplet. For example, when using a high-pressure microfluidic homogenizer, a liquid pressure is typically adjusted to be above about 5,000 psi and a microfluidic channel dimension of a Y-type interaction chamber is chosen to be less than about 100 microns.

In an embodiment of the current invention, said controls and geometries of said second emulsification device are adjusted to cause a high degree of droplet coalescence, so that a droplet of said first drug-loaded oil coalesces with (i.e. combines with) a droplet of said second drug-loaded oil to form a double drug-loaded oil droplet of said first and second drug-loaded oils.

In an embodiment of the current invention, said second emulsification device causes sufficient droplet coalescence to cause the formation of predominantly double drug-loaded oil droplets.

In an embodiment of the current invention, said second emulsification device is a high-pressure microfluidic homogenizer that creates extreme flow stresses (e.g. shear and/or extensional stresses) that overcome interfacial repulsions between droplet interfaces populated with adsorbed stabilizer molecules, yielding substantial droplet coalescence, irrespective of the type of oils inside the droplets.

In an embodiment of the current invention, the type of interfacial structure within said double drug-loaded oil droplet containing said first and said second drug-loaded oils, resulting from at least a droplet coalescence event caused by said second emulsification device, is at least one of a linear Janus droplet (corresponding to an (O1-O2)/W emulsion) and a double-engulfed oil droplet (corresponding to a (O1/O2)/W emulsion).

In an embodiment of the current invention, beyond causing at least some droplet coalescence, said second emulsification device also causes droplet rupturing of at least one of said first droplet of said first drug-loaded oil, said second droplet of said second drug-loaded oil, and said double drug-loaded droplet. For example, if said second emulsification device is a high-pressure microfluidic homogenizer, then said high-pressure microfluidic homogenizer produces high enough flow stresses to cause bigger droplets, including combined double-droplets resulting from coalescence, to rupture into smaller droplets, including combined double-droplets, via a capillary instability. Because continuing droplet coalescence events in said second emulsification device necessary cause the resulting combined droplets to increase in size by volume conservation, then such larger droplets may be more easily ruptured by said second emulsification device (e.g. as rupturing driven via a flow-induced capillary instability that overcomes a droplet Laplace pressure, such as has been described by G. I. Taylor and others), thereby preventing coarsening of the emulsion's size distribution and growth in the average droplet radius.

In an embodiment of the current invention, said double drug-loaded oil droplet is a Janus droplet having at least one of a lens interface and an engulfed droplet interface, such that a maximum dimension of said double drug-loaded oil droplet is less than about five hundred nanometers.

In an embodiment of the current invention, the type of interfacial structure within said double drug-loaded oil droplet containing said first and second drug-loaded oils is selected by at choosing oil 1 (O1), oil 2 (O2), and an aqueous continuous phase which may contain stabilizing molecules, wherein at least one of a O1-O2 interfacial tension, a O1-continuous phase interfacial tension, a O2-continuous phase interfacial tension, a O1-O2-continuous phase line tension, causes a selection of a preferred interfacial structure of said double-loaded oil droplet.

In an embodiment of the current invention, subsequent to said coalescence of said drug-loaded droplets induced by said second emulsification device, the resulting said double drug-loaded oil droplets remain stable against coalescence when subjected to quiescent thermal excitations.

In an embodiment of the current invention, the temperature of said second emulsification device is controlled to prevent heating of said composite premix emulsion being processed into said double drug-loaded oil droplets beyond a desired temperature in order to preserve the efficacy of at least one of said drug molecules in at least one of said drug-loaded oils.

In an embodiment of the current invention, subsequent to at least said droplet coalescence induced by said second emulsification device, an average maximum droplet dimension of said double drug-loaded droplets is less than one micron, yielding a submicron double drug-loaded emulsion.

In an embodiment of the current invention, subsequent to at least said droplet coalescence induced by said second emulsification device, an average maximum droplet dimension of said double drug-loaded droplets is less than two hundred nanometers, yielding a nanoscale double drug-loaded emulsion.

In an embodiment of the current invention, at least one of said first and second oils is at least one of a hydrocarbon oil, an aliphatic oil, a partially aliphatic oil, an aromatic oil, a partially aromatic oil, a silicone oil, a siloxane oil, a partially siloxane oil, a poly-siloxane oil, a halogenated oil, a partially halogenated oil, a fluorinated oil, a fluorinated silicone oil, a fluorinated hydrocarbon oil, a chlorinated oil, a brominated oil, an iodized oil, a plant oil, an animal oil, a fungus oil, a fish oil, a nut oil, a seed oil, a copolymer oil, a branched polymer oil, a branched copolymer oil, a distilled oil, a purified oil, a sterilized oil, a blended oil, a derivatized oil, an anisotropic oil, a lyotropic liquid crystal, a thermotropic liquid crystal, a ferrofluid oil, a nanoparticle-dispersed oil, a non-polar oil, and a polar oil. Specific examples of such oils are listed in product catalogs of companies such as Sigma-Aldrich, Gelest, Cambridge Isotopes, Merck, DuPont, and Cargill.

In an embodiment of the current invention, at least one of said first and second oils is selected to confer a property of at least partial solubility to at least high solubility of at least one of said first and said second drug molecules in at least one of said first and second oils at standard temperature and pressure.

In an embodiment of the current invention, at least one of said stabilizing molecules is at least one of an amphiphilic molecule, a surfactant molecule, a halogenated surfactant molecule, an ionic surfactant molecule, a non-ionic surfactant molecule, a zwitterionic surfactant molecule, a polymeric surfactant molecule, a di-block copolymer molecule, a tri-block copolymer molecule, a pluronic molecule, a poly-ethyleneglycol (PEG) containing molecule, a fluorinated surfactant molecule, an amphiphilic cluster, an amphiphilic siloxane molecule, a protein molecule, a membrane protein molecule, a cell-targeting protein molecule, an antibody molecule, an antigen molecule, and a lipid molecule.

In an embodiment of the current invention, a rate of droplet coalescence (i.e. fusion) in said second emulsification device is controlled through at least one of a type of stabilizer molecules, a concentration of stabilizer molecules, a temperature, a microfluidic geometry, a microfluidic channel dimension, a total droplet volume fraction, an average droplet dimension, an applied pressure, an applied flow stress, and an applied flow rate.

In an embodiment of the current invention, a rate of droplet rupturing (i.e. fission) in said second emulsification device is controlled through at least one of a type of stabilizer molecules, a concentration of stabilizer molecules, a temperature, a microfluidic geometry, a microfluidic channel dimension, a total droplet volume fraction, an average droplet dimension, an applied pressure, an applied flow stress, and an applied flow rate.

In an embodiment of the current invention, an aqueous dispersion of double drug-loaded oil droplets is a nanoscale double drug-loaded emulsion, wherein each droplet has the capacity to co-locally deliver said first, second, and third drug molecules to at least one of a virus, a sub-cellular biological structure, a nucleus of a biological cell, a cytoplasm of a biological cell, a biological membrane, a biological tissue, a biological organ, a biological organism, and a biological colony.

In an embodiment of the current invention, at least one of said first and second oils is loaded with at least one of an imaging contrast enhancement agent, an isotopic molecule, a radioisotopic molecule, an acidic molecule, a basic molecule, at bio-regulating molecule, a molecular complex, a fluorescent molecule, a vitamin molecule, a nutrient molecule, a endocytosis-inducing agent, an apoptosis-inducing agent, a hydrophobic peptide, a hydrophobic polypeptide, a block co-polypeptide that has at least a hydrophobic block, and a hydrophobic protein.

In an embodiment of the current invention said imaging contrast enhancement agent is suitable for detection by at least one of nuclear magnetic resonance, positron emission tomography, x-ray imaging, ultrasonic imaging, electromagnetic imaging, optical fluorescence imaging, and optical scattering.

In an embodiment of the current invention, a first drug-loaded oil is at least a partially fluorinated oil that is loaded with at least a fluorinated drug molecule.

In an embodiment of the current invention, a first drug-loaded oil is an iso-alkane that is loaded with at least an aliphatic drug molecule.

In an embodiment of the current invention, a first drug molecule is at least one of an anti-inflammatory drug molecule, a bio-regulating drug molecule, an anti-microbial drug molecule, an anti-cancer drug molecule, an anti-cholesterol drug molecule, an anti-septic drug molecule, an anti-metabolite molecule, a nutrient molecule, an inhibitor molecule, a promoter molecule, a hydrophobic protein molecule, a hydrophobic amino acid molecule, a hydrophobic poly-amino acid molecule, and a steroid molecule.

In an embodiment of the current invention, a first drug molecule is a steroid molecule. Examples of steroid molecules include but are not limited to the following: a sterol molecule, a steroid hormone molecule, a corticosteroid molecule, an anabolic steroid molecule, a glucocorticoid molecule, a mineralocorticoid molecule, a testosterone molecule, an androgen molecule, an estrogen molecule, a progestogen molecule, an ectdysteroid molecule, a phytosterol molecule, a brassinosteroid molecule, a steroidal alkyloid molecule, and a ergosterol molecule.

In an embodiment of the current invention, a second drug molecule is an anti-microbial drug molecule. Examples of anti-microbial drug molecules include but are not limited to: an anti-biotic molecule, an anti-fungal molecule, an anti-viral molecule, an anti-septic molecule, an anti-microbial peptide, an anti-microbial polypeptide, and an anti-bacterial molecule.

In an embodiment of the current invention, a second drug molecule is an anti-cancer drug molecule that is at least partially hydrophobic. Examples of anti-cancer drug molecules are listed at the National Institute of Health's website: http://www.cancer.gov/cancertopics/druginfo/alphalist.
Such anti-cancer drug molecules include but are not limited to: a paclitaxel, a 5-fluorouracil, a hydroxycamptothecin, a doxorubicin, a cisplatin, a daunorubicin, an etopopside, a vinblastine, a vincristine, a mercaptopurine, and a methotrexate.

Other Alternative Embodiments

In an embodiment of the current invention, at least one of said first, second, and third drug-loaded oils has a viscosity that is reduced by mixing a lower-molecular-weight, volatile, partially water-soluble, and oil-miscible solvent that is miscible with at least one of said first, second, and third drug-loaded oils, and evaporating said solvent subsequent to said droplet coalescence induced by said second emulsification device. In an embodiment of the current invention, said evaporating said solvent causes at least a change in an interfacial curvature of at least one of an internal oil-oil interface and an external oil-water interface of at least one of a double drug-loaded droplet and a triple drug-loaded droplet.

In an embodiment of the current invention at least a first internal oil-oil interface of said triple drug-loaded droplet is deformed by the presence of a second internal oil-oil interface.

In an embodiment of the current invention, an emulsion that contains a multi-component compartmentalized droplets that have at least one of a Janus and Cerberus structure, produced by an energetic excitation that overcomes an interfacial repulsion as has been described herein, is administered to at least one of a human and an animal patient by at least one of the following methods: injecting said emulsion, intravenously injecting said emulsion, inhaling a mist made using said emulsion, spraying topically a mist made using said emulsion, contacting said emulsion to mucosa, contacting topically said emulsion to skin, ocular topical application, nasal topical application, inserting a suppository containing said emulsion, ingesting said emulsion, and ingesting a digestible capsule containing said emulsion.

In an embodiment of the current invention, more than one type of stabilizing molecule is used to alter the interfacial repulsion between droplets, thereby changing the strength of an athermal energetic excitation required to produce coalescence between droplets.

In an embodiment of the current invention, at least a concentration of a stabilizing molecule is adjusted to alter the interfacial repulsion between droplets, thereby changing the strength of an athermal energetic excitation required to produce coalescence between droplets.

In an embodiment of the current invention, at least one type of oil in an emulsion of multi-component compartmentalized droplets provides a moisturizing effect to skin.

In an embodiment of the current invention, at least one type of oil in an emulsion of multi-component compartmentalized droplets provides a beneficial nutritional effect when ingested.

In an embodiment of the current invention, an interfacial targeting molecule is added to the composition of an emulsion of drug-loaded multi-component compartmentalized droplets to coat said droplets, thereby causing said interfacial-coated droplets to target and accumulate in a particular desired tissue in a patient.

In an embodiment of the current invention, a multi-oil-component premix emulsion contains microscale or larger multi-component compartmentalized oil droplets, which are ruptured by the strong applied athermal excitations down to an average maximum dimensions that is at least one of a submicron and a nanoscale dimension.

In an embodiment of the current invention, a multi-oil-component premix emulsion contains at least two different oil types of single-component oil droplets, wherein said single-component oil droplets have at least one of submicron and nanoscale dimensions, wherein said strong applied athermal excitations cause substantially only fusion of droplets by overcoming an interfacial repulsive barrier but not rupturing of droplets to produce at least an emulsion containing multi-component compartmentalized oil droplets that remain stable under quiescent thermal excitations after said strong applied athermal excitations are removed.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

In some embodiments, the diagnostic materials do not necessarily have to be biologically active agents (e.g. isotopes, contrast enhancement agents, fluorescent dyes, etc).

In some embodiments, a stabilizer can be a surfactant and is efficacious at stabilizing the exposed surfaces of the plurality of droplets over a range of temperatures and a range of flow rates. It is not obvious that a given surfactant type can effectively stabilize all surfaces of a fused droplets to prevent coalescence subsequent to forming the fused droplets.

In some embodiments, a first flow rate that is below about $10^3$ $s^{-1}$ that does not rupture or cause coalescence of droplets can be used. A subsequent flow rate with a maximum strain rate of flow above a certain value (e.g. about $10^5$ $s^{-1}$) and/or that can causes both droplet coalescence and droplet rupturing can be employed.

In some embodiments, a processed emulsion can be recirculated through a microfluidic device many times, so it sees the same rupturing environment multiple times. This improves the overall uniformity of the morphologies of the resulting fused droplets.

In some embodiments, "liquid", "liquid medium", or "liquid phase", whether internal or external, could be intended to mean a liquid solution (e.g. of small molecule drugs or macromolecules) or could be intended to mean a liquid-based dispersion of fine nanoscale objects that are much smaller than a maximum spatial dimension of any resulting internal droplet structures.

In addition, although coalescence is commonly used in the field of emulsions to refer to merging or fusion of two or more droplets having the same type of internal droplet liquid or at least two types of droplet liquids that are miscible, here, coalescence can refer to merging or fusion of two or more droplets that can have different types of internal droplet liquids, including internal droplet liquids that are immiscible.

REFERENCES

1. Becher, P., ed. *Encyclopedia of Emulsion Technology*; Marcel Dekker, Inc.: New York, 1996.
2. Fryd, M. M.; Mason, T. G. Time-Dependent Nanoemulsion Droplet Size Reduction by Evaporative Ripening. *J. Phys. Chem. Lett.* 2010, 1, 3349-3353.
3. van Aken, G. A.; Zoet, F. D. Coalescence in Highly Concentrated Coarse Emulsions. *Langmuir* 2000, 16, 7131-7138.
4. Niu, X.; Gielen, F.; deMello, A. J.; Edel, J. B. Electro-Coalescence of Digitally Controlled Droplets. *Anal. Chem.* 2009, 81, 7321-7325.
5. Eow, J. S.; Ghadiri, M.; Sharif, A. O.; Williams, T. J. Electrostatic Enhancement of Coalescence of Water Droplets in Oil: A Review of the Current Understanding. *Chem. Eng. J.* 2001, 84, 173-192.
6. Jafari, S. M.; Assadpoor, E.; He, Y.; Bhandari, B. Re-Coalescence of Emulsion Droplets During High-Energy Emulsification. *Food Hydrocolloids* 2008, 22, 1191-1202.
7. Tan, Y.-C.; Ho, Y. L.; Lee, A. P. Droplet Coalescence by Geometrically Mediated Flow in Microfluidic Channels. *Microfluid Nanofluid* 2007, 3, 495-499.
8. Boyd, J.; Parkinson, C.; Sherman, P. Factors Affecting Emulsion Stability, and the HLB Concept. *J. Colloid Interface Sci.* 1971, 41, 359-370.
9. Tcholakova, S.; Denkov, N. D.; Ivanov, I. B.; Campbell, B. Coalescence Stability of Emulsions Containing Globular Milk Proteins. *Adv. Colloid Interface Sci.* 2006, 123-126, 259-293.
10. Mason, T. G.; Wilking, J. N.; Meleson, K.; Chang, C. B.; Graves, S. M. Nanoemulsions: Formation, Structure, and Physical Properties. *J. Phys.: Condens. Matter* 2006, 18, R635-R666.
11. Leal, L. G. Flow Induced Coalescence of Drops in a Viscous Fluid. *Phys. Fluids* 2004, 16, 1833-1851.
12. Torza, S.; Mason, S. G. Three-Phase Interactions in Shear and Electrical Fields. *J. Colloid Interface Sci.* 1970, 33, 67-83.
13. Torza, S.; Mason, S. G. Effects of the Line Tension on 3-Phase Liquid Interactions. *Kolloid-Z. u. Z. Polymere* 1971, 246, 593-599.
14. Thiam, A. R.; Bremond, N.; Bibette, J. Adhesive Emulsion Bilayers under an Electric Field: From Unzipping to Fusion. *Phys. Rev. Lett.* 2011, 107, 068301.
15. Hasinovic, H.; Friberg, S. E. One-Step Inversion Process to a Janus Emulsion with Two Mutually Insoluble Oils. *Langmuir* 2011, 27, 6584-6588.
16. Manoharan, V. N.; Elsesser, M. T.; Pine, D. J. Dense Packing and Symmetry in Small Clusters of Microspheres. *Science* 2003, 301, 483-487.
17. Mayoral, K.; Kennair, T. P.; Zhu, X.; Milazzo, J.; Ngo, K.; Fryd, M. M.; Mason, T. G. Rotational Fourier Tracking of Diffusing Polygons. *Phys. Rev. E* 2011, 84, 051405.
18. Kraft, D. J.; Vlug, W. S.; van Kats, C. M.; van Blaaderen, A.; Imhof, A.; Kegel, W. K. Self-Assembly of Colloids with Liquid Protrusions. *J. Am. Chem. Soc.* 2008, 131, 1182-1186.
19. Jiang, T.; Zukoski, C. F. Synthesis of pH-Responsive Particles with Shape Anisotropy. *Langmuir* 2012, 28, 6760-6768.
20. Fryd, M. M.; Mason, T. G. Advanced Nanoemulsions. *Annu. Rev. Phys. Chem.* 2012, 63, 493-518.
21. Tadros, T.; Izquierdo, P.; Esquena, J.; Solans, C. Formation and Stability of Nano-Emulsions. *Adv. Colloid Interface Sci.* 2004, 108-109, 303-318.
22. Gutiérrez, J. M.; González, C.; Maestro, A.; Solè, I.; Pey, C. M.; Nolla, J. Nano-Emulsions: New Applications and Optimization of Their Preparation. *Curr. Opin. Colloid Interface Sci.* 2008, 13, 245-251.
23. Solans, C.; Izquierdo, P.; Nolla, J.; Azemar, N.; Garcia-Celma, M. J. Nano-Emulsions. *Curr. Opin. Colloid Interface Sci.* 2005, 10, 102-110.
24. Fryd, M. M.; Mason, T. G. Nanoinclusions in Cryogenically Quenched Nanoemulsions. *Langmuir* 2012, 28, 12015-12021.
25. Meleson, K.; Graves, S.; Mason, T. G. Formation of Concentrated Nanoemulsions by Extreme Shear. *Soft Mater.* 2004, 2, 109-123.
26. Israelachvili, J. N. Intermolecular and Surface Forces, *Elsevier*, New York, 3rd edn., 2011.
27. Taylor, P. *Adv. Colloid Interface Sci.*, 1998, 75, 107-163.
28. Lee, D. J. *Colloid Polym. Sci.*, 1995, 273, 539-543.
29. Wilking, J. Mason, T. G. *Phys. Rev. E*, 2007, 75, 041407.
30. Graves, S. M.; Mason, T. G. *J. Phys. Chem. C*, 2008, 112, 12669-12676.
31. Zhu, X.; Fryd, M. M.; Huang, J.-R.; Mason, T. G. *Phys. Chem. Chem. Phys.*, 2012, 14, 2455-2461.
32. Bibette, J.; Mason, T. G.; Gang, H.; Weitz, D. A.; Poulin, P. *Langmuir*, 1993, 9, 3352-3356.
33. Mollet, H.; Grubenmann, A.; *Formulation Technology: Emulsions, Suspensions, Solid Forms*, Wiley-VCH, Weinheim, 2001.
34. Myers, D. *Surfaces, Interfaces, and Colloids*, VCH Publishers, New York, 1991.
35. Shiloach, A.; Blankschtein, D. *Langmuir*, 1998, 1998, 1618-1636.
36. Kaler, E. W.; Murthy, A. K.; Rodriguez, B. E.; Zasadzinski, J. A. *Science*, 1989, 245, 1371-1374.
37. Yatcilla, M. T.; Herrington, K. L.; Brasher, L. L.; Kaler, E. W.; Chiruvolu, S.; Zasadzinski, J. A. *J. Phys. Chem.*, 1996, 100, 5874-5879.
38. Chen, L.; Xiao, J.-X.; Ruan, K.; Ma, J. *Langmuir*, 2002, 18, 7250-7252.
39. Lucassen-Reynders, E. H. *J. Colloid Interface Sci.*, 1981, 81, 150-157.
40. Fainerman, V. B.; Lucassen-Reynders, E. H. *Adv. Colloid Interface Sci.*, 2002, 96, 295-323.
41. Herrington, K. L.; Kaler, E. W.; Miller, D. D.; Zasadzinski, J. A.; Chiruvolu, S. *J. Phys. Chem.*, 1993, 97, 13792-13802.
42. Kaler, E. W.; Herrington, K. L.; Murthy, A. K.; Zasadzinski, J. A. N. *J. Phys. Chem.*, 1992, 96, 6698-6707.
43. Hafez, I. M.; Ansell, S.; Cullis, P. R. *Biophys J.*, 2000, 79, 1438-1446.
44. Fryd, M. M.; Mason, T. G. *Langmuir*, 2013, 29, 15787-15793.
45. Kim, J. H.; Jeon, T. Y.; Choi, T. M.; Shim, T. S.; Kim, S.-H.; Yang, S.-M. *Langmuir*, 2014, 30, 1473-1488.
46. Choi, C.-H.; Weitz; D. A.; Lee, C.-S. *Adv. Mat.*, 2013, 25, 2536-2541.
47. Nie, Z.; Li, W.; Seo, M.; Xu, S.; Kumacheva, E. *J. Am. Chem. Soc.*, 2006, 128, 9408-9412.
48. Chen, C.-H.; Shah, R. K.; Abate, A. R.; Weitz, D. A. *Langmuir*, 2009, 25, 4320-4323.
49. S.-Y. Teh, R. Lin, L.-H. Hung, A. P. Lee, *Lab Chip*, 2008, 8, 198-220.

We claim:
1. An emulsion, comprising:
a continuous liquid medium; and
a plurality of droplets dispersed in said continuous liquid medium, wherein each of said plurality of droplets comprises a first droplet liquid and a second droplet liquid, wherein said first and second droplet liquids are immiscible with each other and immiscible with said continuous liquid medium such that each of said plurality of droplets has at least a first interface of contact between said first droplet liquid and second droplet liquid, wherein said plurality of droplets has an ensemble-average maximal spatial dimension that is less than 1 µm, and wherein said continuous liquid medium has a region of contact with at least a portion of said at least a first interface of contact between said first and second droplet liquids.

2. An emulsion according to claim 1, wherein said plurality of droplets has an ensemble-average maximal spatial dimension that is less than 300 nanometers.

3. An emulsion according to claim 1, wherein said plurality of droplets has an ensemble-average maximal spatial dimension that is between 15 nanometers and 150 nanometers.

4. An emulsion according to claim 1, further comprising a stabilizer that is efficacious at adsorbing to and stabilizing an external interface of contact between said continuous liquid medium and at least one of said first droplet liquid and said second droplet liquid of said plurality of droplets with a repulsive interdroplet interaction over a range of temperatures and a range of flow rates.

5. An emulsion according to claim 1, wherein each of said plurality of droplets comprises a third droplet liquid, and wherein said third droplet liquid is immiscible with said first and second droplet liquids and is immiscible with said continuous liquid medium such that each of said plurality of droplets has at least a second interface of contact between said third droplet liquid and at least one of said first and second droplet liquids.

6. An emulsion according to claim 5, wherein said plurality of droplets has an ensemble-average maximal spatial dimension that is less than 300 nanometers.

7. An emulsion according to claim 5, wherein said plurality of droplets has an ensemble-average maximal spatial dimension that is between 15 nanometers and 150 nanometers.

8. An emulsion according to claim 5, wherein at least one of said first, second and third droplet liquids in each of said plurality of droplets is engulfed therein so as to have no direct contact with said continuous liquid medium.

9. The emulsion of claim 5, wherein said emulsion does not comprise an amphiphilic block co-polymer as a stabilizing molecule, and wherein said amphiphilic block co-polymer comprises a hydrophilic polymer block and a hydrophobic polymer block.

10. The emulsion of claim 5, wherein said at least second interface of contact between said third droplet liquid and at least one of said first and second droplet liquids is non-spherical in shape.

11. An emulsion according to claim 1, further comprising:
a first solute material dissolved in said first droplet liquid; and
a second solute material dissolved in said second droplet liquid,
wherein said first solute material is more soluble in said first droplet liquid than in said second droplet liquid, and
wherein said second solute material is more soluble in said second droplet liquid than in said first droplet liquid.

12. An emulsion according to claim 11, wherein said first and second solute materials are a first and a second biologically active materials.

13. An emulsion according to claim 11, wherein said first and second solute materials are at least one of a therapeutic, a diagnostic or a nutritional material.

14. The emulsion of claim 1, wherein said emulsion does not comprise an amphiphilic block co-polymer as a stabilizing molecule.

15. The emulsion of claim 1, wherein said emulsion does not comprise an amphiphilic block co-polymer as a stabilizing molecule, and wherein said amphiphilic block co-polymer comprises a hydrophilic polymer block and a hydrophobic polymer block.

16. A nanoemulsion, comprising:
a continuous liquid medium; and
a plurality of droplets dispersed in said continuous liquid medium,
wherein each of said plurality of droplets comprises a first droplet liquid, a second droplet liquid and a third droplet liquid,
wherein said first, second and third droplet liquids are immiscible with each other and immiscible with said continuous liquid medium such that each of said plurality of droplets has at least a first interface of contact between said first droplet liquid and second droplet liquid and at least a second interface of contact between said third droplet liquid and at least one of said first and second droplet liquids, and
wherein said continuous liquid medium has a region of contact with at least a portion of said at least a first interface of contact between said first and second droplet liquids.

17. A method of forming an emulsion, comprising:
obtaining a first emulsion comprising a first continuous liquid medium and a plurality of first droplets of a first droplet liquid dispersed in said first continuous liquid medium;
obtaining a second emulsion comprising a second continuous liquid medium and a plurality of second droplets of a second droplet liquid dispersed in said second continuous liquid medium;
mixing said first and second emulsions to provide a mixed emulsion wherein said first and second droplets are stabilized by an interfacial repulsion against forming an interface of contact between said first and second droplet liquids in a common mixed continuous liquid medium while experiencing quiescent thermal excitations; and
subjecting said mixed emulsion to an athermal energetic excitation sufficient to overcome an interfacial repulsion between at least a first droplet of said first emulsion and a second droplet of said second emulsion to form a resultant emulsion comprising a plurality of droplets comprising said first droplet liquid and said second droplet liquid having at least a first interface of contact between said first and second droplet liquids,
wherein said first and second droplet liquids are immiscible with each other and immiscible with said continuous liquid medium,
wherein said plurality of droplets has an ensemble-average maximal spatial dimension that is less than 1 µm, and wherein said continuous liquid medium has a region of contact with at least a portion of said at least a first interface of contact between said first and second droplet liquids.

18. The method of forming an emulsion according to claim 17, wherein said plurality of droplets has an ensemble-average maximal spatial dimension that is less than 300 nanometers.

19. The method of forming an emulsion according to claim 17, wherein said plurality of droplets has an ensemble-average maximal spatial dimension that is between 15 nanometers and 150 nanometers.

20. The method of forming an emulsion according to claim 17, wherein said at least one of said first emulsion and said second emulsion is a nanoemulsion.

21. The method of forming an emulsion according to claim 17, further comprising:
dissolving a first solute material into said first droplet liquid prior to obtaining said first emulsion;
dissolving a second solute material into said second droplet liquid prior to obtaining said second emulsion;
wherein said first solute material is more soluble in said first droplet liquid than in said second droplet liquid, and
wherein said second solute material is more soluble in said second droplet liquid than in said first droplet liquid.

22. The method of forming an emulsion according to claim 21, wherein said first and second solute materials are a first and a second biologically active materials.

23. The method of forming an emulsion according to claim 21, wherein said first and second solute materials each are at least one of a therapeutic, a diagnostic or a nutritional material.

24. The method of forming an emulsion according to claim 17, further comprising:
adding one of an anionic amphiphilic agent or a cationic amphiphilic agent to said first emulsion and said second emulsion; and
adding a preselected amount of an ionic agent that is oppositely charged as said one of said anionic amphiphilic agent or said cationic amphiphilic agent to said resultant emulsion such that at least some of said plurality of droplets further coalesce to provide a resultant emulsion comprising a plurality of further coalesced droplets.

25. The method of forming an emulsion according to claim 17, further comprising:
obtaining an intermediate emulsion, said intermediate emulsion comprising:
said resultant emulsion comprising a plurality of droplets comprising said first droplet liquid and said second droplet liquid having at least a first interface of contact between said first and second droplet liquids,
a third continuous liquid medium,
a third plurality of droplets of a third droplet liquid dispersed in said third continuous liquid medium, and
one of an anionic amphiphilic agent or a cationic amphiphilic agent; and
adding a preselected amount of an ionic agent that is oppositely charged as said one of said anionic amphiphilic agent or said cationic amphiphilic agent such that at least some of said plurality of droplets comprising said first droplet liquid and said second droplet liquid having at least a first interface of contact between said first and second droplet liquids and said third plurality of droplets coalesce to provide a second resultant emulsion comprising a plurality of coalesced droplets,
wherein said first, second and third droplet liquids are immiscible with each other and immiscible with said continuous liquid medium such that each of said plurality of coalesced droplets has segmented first droplet liquid, second droplet liquid and third droplet liquid sections.

26. A method of forming an emulsion, comprising:
obtaining a precursor emulsion, said precursor emulsion comprising:
a continuous liquid medium,
a first plurality of droplets of a first droplet liquid dispersed in said continuous liquid medium,
a second plurality of droplets of a second droplet liquid dispersed in said continuous liquid medium, and
one of an anionic amphiphilic agent or a cationic amphiphilic agent; and
adding a preselected amount of an ionic agent that is oppositely charged as said one of said anionic amphiphilic agent or said cationic amphiphilic agent such that at least some of said first plurality of droplets and said second plurality of droplets coalesce to provide a resultant emulsion comprising a plurality of coalesced droplets,
wherein said first and second droplet liquids are immiscible with each other and immiscible with said continuous liquid medium such that each of said plurality of coalesced droplets has segmented first droplet liquid and second droplet liquid sections and such that each of said plurality of droplets has at least a first interface of contact between said first droplet liquid and second droplet liquid,
wherein said plurality of droplets has an ensemble-average maximal spatial dimension that is less than 1 µm, and
wherein said continuous liquid medium has a region of contact with at least a portion of said at least a first interface of contact between said first and second droplet liquids.

27. The method of forming an emulsion according to claim 26, wherein said plurality of droplets has an ensemble-average maximal spatial dimension that is less than 300 nanometers.

28. The method of forming an emulsion according to claim 26, wherein said plurality of droplets has an ensemble-average maximal spatial dimension that is between 15 nanometers and 150 nanometers.

29. The method of forming an emulsion according to claim 26, wherein said coalesced droplets of said resultant emulsion are at least one of Janus droplets, Cerberus droplets, or higher order droplets.

30. The method of forming an emulsion according to claim 26, further comprising:
dissolving a first solute material into said first droplet liquid prior to obtaining said precursor emulsion;
dissolving a second solute material into said second droplet liquid prior to obtaining said precursor emulsion;
wherein said first solute material is more soluble in said first droplet liquid than in said second droplet liquid, and
wherein said second solute material is more soluble in said second droplet liquid than in said first droplet liquid.

31. The method of forming an emulsion according to claim 30, wherein said first and second solute materials are a first and a second biologically active materials.

32. The method of forming an emulsion according to claim 30, wherein said first and second solute materials each are at least one of a therapeutic, a diagnostic or a nutritional material.

\* \* \* \* \*